(12) United States Patent
Holland et al.

(10) Patent No.: US 11,246,754 B2
(45) Date of Patent: *Feb. 15, 2022

(54) SURGICAL SYSTEM AND PROCEDURE FOR TREATMENT OF THE TRABECULAR MESHWORK AND SCHLEMM'S CANAL USING A FEMTOSECOND LASER

(71) Applicant: ViaLase, Inc., Aliso Viejo, CA (US)

(72) Inventors: Guy Holland, San Juan Capistrano, CA (US); Tibor Juhasz, San Clemente, CA (US); Wesley W. Lummis, Rancho Santa Margarita, CA (US); Eric R. Mikula, Aliso Viejo, CA (US); Ferenc Raksi, Mission Viejo, CA (US); Manu Sharma, Ladera Ranch, CA (US); Carlos G. Suarez, Tustin, CA (US)

(73) Assignee: VIALASE, INC., Aliso Viejo, CA (US)

(*) Notice: Subject to any disclaimer, the term of this patent is extended or adjusted under 35 U.S.C. 154(b) by 124 days.

This patent is subject to a terminal disclaimer.

(21) Appl. No.: 16/674,850

(22) Filed: Nov. 5, 2019

(65) Prior Publication Data

US 2020/0078218 A1    Mar. 12, 2020

Related U.S. Application Data

(63) Continuation-in-part of application No. 16/125,588, filed on Sep. 7, 2018, now Pat. No. 11,110,006, and
(Continued)

(51) Int. Cl.
*A61F 9/008* (2006.01)

(52) U.S. Cl.
CPC .............. *A61F 9/00825* (2013.01); *A61F 2009/00855* (2013.01); *A61F 2009/00868* (2013.01); *A61F 2009/00891* (2013.01)

(58) Field of Classification Search
CPC .............. A61F 9/00825; A61F 9/00781; A61F 9/0084; A61F 2009/00851;
(Continued)

(56) References Cited

U.S. PATENT DOCUMENTS 6,251,103 B1    6/2001   Berlin
6,482,199 B1   11/2002   Neev
(Continued)

FOREIGN PATENT DOCUMENTS

CN      104382689 B    9/2016
EP        1080706 A1   3/2001
(Continued)

OTHER PUBLICATIONS

PCT/US2019/042553, IPEA Written Opinon (dated Jul. 20, 2020).
(Continued)

*Primary Examiner* — Mark W. Bockelman
(74) *Attorney, Agent, or Firm* — Loza & Loza, LLP; David S. Sarisky

(57) ABSTRACT

A target volume of ocular tissue is treated with a laser having a direction of propagation toward the target volume, where the target volume is characterized by a distal extent, a proximal extent, and a lateral extent. A layer of tissue at an initial depth corresponding to the distal extent of the target volume is initially photodisrupted using a femtosecond laser by scanning the laser in multiple directions defining an initial treatment plane. Tissue at one or more subsequent depths between the distal extent of the target volume and the proximal extent of the target volume is subsequently photodisrupted using a femtosecond laser by moving a focus of the laser in a direction opposite the direction of propagation of the laser and then scanning the laser in multiple directions defining an subsequent treatment plane. Photodisruption is
(Continued)

repeated at different subsequent depths until tissue at the proximal extent of the target volume is photodisrupted.

14 Claims, 25 Drawing Sheets

Related U.S. Application Data a continuation-in-part of application No. 16/036,833, filed on Jul. 16, 2018, now Pat. No. 10,821,023.

(58) Field of Classification Search
CPC .. A61F 2009/00855; A61F 2009/00868; A61F 2009/00872; A61F 2009/00897; A61F 2009/00891
See application file for complete search history.

(56) References Cited

U.S. PATENT DOCUMENTS

| | | |
|---|---|---|
| 6,682,523 B2 | 1/2004 | Shadduck |
| 6,989,007 B2 | 1/2006 | Shadduck |
| 7,131,968 B2 | 11/2006 | Bendett et al. |
| 7,192,412 B1 | 3/2007 | Zhou et al. |
| 7,282,046 B2 | 10/2007 | Simon |
| 7,351,241 B2 | 4/2008 | Bendett et al. |
| 8,011,504 B1 | 9/2011 | Farberov |
| 8,171,937 B2 | 5/2012 | Bendett et al. |
| 8,230,866 B2 | 7/2012 | Hauger et al. |
| 8,523,926 B2 | 9/2013 | Neev |
| 8,540,659 B2 | 9/2013 | Berlin |
| 8,568,393 B2 | 10/2013 | Palanker |
| 8,679,089 B2 | 3/2014 | Berlin |
| 8,687,866 B2 | 4/2014 | Marziliano et al. |
| 8,845,624 B2 | 9/2014 | Raksi et al. |
| 8,920,407 B2 | 12/2014 | Raksi et al. |
| 9,033,963 B2 | 5/2015 | Vera et al. |
| 9,044,303 B2 | 6/2015 | Kurtz et al. |
| 9,259,153 B2 | 2/2016 | Goto |
| 9,265,411 B2 | 2/2016 | Chen et al. |
| 9,320,650 B2 | 4/2016 | Bendett et al. |
| 9,441,946 B2 | 9/2016 | Massow et al. |
| 9,456,925 B2 | 10/2016 | Kurtz et al. |
| 9,498,295 B2 | 11/2016 | Palanker |
| 9,517,006 B2 | 12/2016 | Izatt et al. |
| 9,554,702 B2 | 1/2017 | Papac et al. |
| 9,603,741 B2 | 3/2017 | Berlin |
| 9,603,744 B2 | 3/2017 | Hailmann et al. |
| 9,629,750 B2 | 4/2017 | Dambacher et al. |
| 9,642,746 B2 | 5/2017 | Berlin |
| 9,681,985 B2 | 6/2017 | Andersen et al. |
| 9,724,238 B2 | 8/2017 | Heitel |
| 9,750,640 B2 | 9/2017 | Palanker et al. |
| 9,820,883 B2 | 11/2017 | Berlin |
| 9,833,357 B2 | 12/2017 | Berlin |
| 9,844,464 B2 | 12/2017 | Bendett et al. |
| 9,936,868 B2 | 4/2018 | Izatt et al. |
| 10,064,757 B2 | 9/2018 | Berlin |
| 10,073,515 B2 | 9/2018 | Awdeh |
| 10,159,600 B2 | 12/2018 | Horvath et al. |
| 10,159,601 B2 | 12/2018 | Berlin |
| 10,165,941 B2 | 1/2019 | Walsh et al. |
| 10,179,066 B2 | 1/2019 | Badawi et al. |
| 10,195,078 B2 | 2/2019 | Horvath et al. |
| 10,195,079 B2 | 2/2019 | Horvath et al. |
| 10,195,080 B2 | 2/2019 | Berlin |
| 10,238,281 B2 | 3/2019 | Isogai et al. |
| 10,238,541 B2 | 3/2019 | Yee et al. |
| 10,292,868 B2 | 5/2019 | Chew et al. |
| 10,335,314 B2 | 7/2019 | Berlin |
| 10,360,683 B2 | 7/2019 | Iwase et al. |
| 10,362,935 B2 | 7/2019 | Dastmalchi et al. |
| 10,362,936 B2 | 7/2019 | Buckland et al. |
| 10,363,169 B2 | 7/2019 | Belkin et al. |
| 10,363,172 B2 | 7/2019 | Kawai et al. |
| 10,383,689 B2 | 8/2019 | Berlin |
| 10,390,883 B2 | 8/2019 | Deladurantaye et al. |
| 10,398,306 B2 | 9/2019 | Liu |
| 10,406,034 B2 | 9/2019 | Siegele |
| 10,426,548 B2 | 10/2019 | Tearney et al. |
| 10,456,030 B2 | 10/2019 | Buckland et al. |
| 10,456,209 B2 | 10/2019 | Peyman |
| 10,478,060 B2 | 11/2019 | Kubota |
| 10,493,274 B2 | 12/2019 | Irazoqui et al. |
| 10,499,809 B2 | 12/2019 | Kalina, Jr. et al. |
| 10,500,094 B2 | 12/2019 | Buzawa et al. |
| 10,517,760 B2 | 12/2019 | Berlin |
| 10,524,822 B2 | 1/2020 | Aljuri et al. |
| 10,537,476 B2 | 1/2020 | Ha et al. |
| 10,542,883 B2 | 1/2020 | Gooi et al. |
| 10,543,122 B2 | 1/2020 | Kahook |
| 10,596,036 B2 | 3/2020 | Pinchuk |
| 10,603,214 B2 | 3/2020 | Bigler et al. |
| 10,603,216 B2 | 3/2020 | Kurtz et al. |
| 10,653,557 B2 | 5/2020 | Rill et al. |
| 10,674,906 B2 | 6/2020 | Kalina, Jr. et al. |
| 10,687,978 B2 | 6/2020 | Berlin |
| 10,702,416 B2 | 7/2020 | Belkin et al. |
| 10,744,033 B2 | 8/2020 | Baerveldt et al. |
| 10,744,034 B2 | 8/2020 | Homer |
| 10,758,418 B2 | 9/2020 | Vold et al. |
| 10,779,988 B2 | 9/2020 | Fu et al. |
| 10,799,113 B2 | 10/2020 | Vadakke Matham et al. |
| 10,821,023 B2 | 11/2020 | Raksi |
| 10,821,024 B2 | 11/2020 | Raksi |
| 10,888,461 B2 | 1/2021 | Orthaber et al. |
| 2002/0013572 A1 | 1/2002 | Berlin |
| 2004/0070761 A1 | 4/2004 | Horvath et al. |
| 2006/0200113 A1 | 9/2006 | Haffner |
| 2009/0149840 A1 | 6/2009 | Kurtz |
| 2009/0149841 A1 | 6/2009 | Kurtz |
| 2009/0157062 A1 | 6/2009 | Hauger et al. |
| 2010/0130966 A1 | 5/2010 | Brownell |
| 2012/0257167 A1 | 10/2012 | Gille et al. |
| 2012/0259321 A1 | 10/2012 | Vera et al. |
| 2012/0283557 A1 | 11/2012 | Berlin |
| 2012/0303007 A1 | 11/2012 | Loesel et al. |
| 2013/0085484 A1 | 4/2013 | Van Valen et al. |
| 2013/0103011 A1 | 4/2013 | Grant et al. |
| 2013/0237972 A1 | 9/2013 | Raksi |
| 2014/0142599 A1 | 5/2014 | Jeglorz et al. |
| 2014/0216468 A1 | 8/2014 | Goldshleger et al. |
| 2014/0236066 A1 | 8/2014 | Horvath et al. |
| 2014/0288485 A1 | 9/2014 | Berlin |
| 2014/0354951 A1 | 12/2014 | Izatt et al. |
| 2015/0077528 A1 | 3/2015 | Awdeh |
| 2015/0080783 A1 | 3/2015 | Berlin |
| 2015/0157505 A1 | 6/2015 | Neev |
| 2015/0305939 A1 | 10/2015 | Vera et al. |
| 2015/0305940 A1 | 10/2015 | Vera et al. |
| 2015/0313759 A1 | 11/2015 | Vera et al. |
| 2015/0335477 A1 | 11/2015 | Schuele et al. |
| 2015/0359426 A1 | 12/2015 | Buckland et al. |
| 2016/0095751 A1 | 4/2016 | Berlin |
| 2016/0213512 A1 | 7/2016 | Palanker et al. |
| 2016/0220110 A1 | 8/2016 | Vogler et al. |
| 2017/0020732 A1 | 1/2017 | Berlin |
| 2017/0027437 A1 | 2/2017 | Neal et al. |
| 2017/0042736 A9 | 2/2017 | Berlin |
| 2017/0119579 A9 | 5/2017 | Berlin |
| 2017/0127938 A1 | 5/2017 | Izatt et al. |
| 2017/0202708 A1 | 7/2017 | Berlin |
| 2017/0326003 A1 | 11/2017 | Schuele et al. |
| 2018/0028355 A1 | 2/2018 | Raksi |
| 2018/0207029 A1 | 7/2018 | Herekar et al. |
| 2018/0221205 A1 | 8/2018 | Berlin |
| 2018/0235462 A1 | 8/2018 | Gooi et al. |
| 2018/0360310 A1 | 12/2018 | Berlin |
| 2018/0360655 A1 | 12/2018 | Berlin |
| 2019/0083313 A1 | 3/2019 | Berlin |
| 2019/0083314 A1 | 3/2019 | Berlin |
| 2019/0117459 A1 | 4/2019 | Berlin |
| 2020/0078216 A1 | 3/2020 | Raksi |

(56) References Cited

U.S. PATENT DOCUMENTS

| | | |
|---|---|---|
| 2020/0078217 A1 | 3/2020 | Raksi |
| 2020/0078218 A1 | 3/2020 | Holland et al. |
| 2021/0052416 A1 | 2/2021 | Herekar et al. |

FOREIGN PATENT DOCUMENTS

| | | |
|---|---|---|
| EP | 1208792 A1 | 5/2002 |
| EP | 1017308 B1 | 6/2003 |
| EP | 2384727 A1 | 11/2011 |
| WO | 2013188885 A1 | 12/2013 |
| WO | 2017031570 A1 | 3/2017 |
| WO | 2018049246 A1 | 3/2018 |
| WO | 2019173759 A1 | 9/2019 |

OTHER PUBLICATIONS

PCT/US2019/039043, IPEA Written Opinion (dated Aug. 17, 2020).
PCT/US2019/039033, IPEA Written Opinion (dated Jul. 6, 2020).
Junker et al. "Intraoperative optical coherence tomography and ab interno trabecular meshwork surgery with the trabectome." Clin Ophthalmol. 11: 1755-1760 (Sep. 28, 2017).
McNabb et al. "Complete 360° circumferential gonioscopic optical coherence tomography imaging of the iridocorneal angle." Biomedical Optics Express vol. 6, Issue 4, pp. 1376-1391 (2015).
Xin et al. "OCT study of mechanical properties associated with Trabecular meshwork and collector channel motion in human eyes." PLoS One. 2016; 11(9): e0162048. doi: 10.1371/journal.pone. 0162048 (Sep. 6, 2016).
Xin et al. "Aqueous outflow regulation: optical coherence tomography implicates pressure-dependent tissue motion." Experimental Eye Research, vol. 158, pp. 171-186 (May 2017).
PCT/US2019/039033, Int'l Search Report & Written Opinion (dated Oct. 2, 2019).
PCT/US2019/039043, Int'l Search Report & Written Opinion (dated Oct. 10, 2019).
PCT/US2019/042553, Int'l Search Report & Written Opinion (dated Oct. 10, 2019).
PCT/US2019/042571, Int'l Search Report & Written Opinion (dated Oct. 15, 2019).
Brubaker, "Goldmann's equation and clinical measures of aqueous dynamics". Experimental Eye Research, vol. 78, Issue 3, pp. 633-637 (2004).
Grant, "Tonographic method for measuring the facility and rate of aqueous flow in human eyes". Arch. Ophthalmol. 44(2), pp. 204-214 (1950).
Hann et al. "Anatomic changes in schlemm's canal and collector channels in normal and primary open-angle glaucoma eyes using low and high perfusion pressures". Glaucoma, vol. 55:9 (Sep. 2014).
Johnstone, "The aqueous outflow system as a mechanical pump: evidence from examination of tissue and aqueous movement in human and non-human primates". J Glaucoma, vol. 13:5, pp. 421-438 (Oct. 2004).
Jones et al., "New methods of measuring the rate of aqueous flow in man with fluorescein". Experimental Eye Research, vol. 5:3, pp. 208-220 (Jul. 1966).
Kagemann et al. "Characterisation of Schlemm's canal cross-sectional area." Br J Ophthalmol 2014, 98 (Suppl. II) (Mar. 3, 2014).
Rosenquist et al., "Ouflow resistance of enucleated human eyes at two different perfusion pressures and different extents of trabeculotomy". Current Eye Research, vol. 8:12, pp. 1233-1240 (1989).
PCT/US2020/055632, International Search Report & Written Opinion (dated Jan. 27, 2021).
PCT/US2020/055632, IPEA Written Opinion (dated Sep. 13, 2021).

SURGICAL SYSTEM AND PROCEDURE FOR TREATMENT OF THE TRABECULAR MESHWORK AND SCHLEMM'S CANAL USING A FEMTOSECOND LASER

CROSS-REFERENCE TO RELATED APPLICATION(S)

This application is a continuation-in-part of each of U.S. patent application Ser. No. 16/036,833, filed Jul. 16, 2018, for "Integrated Surgical System and Method for Treatment in the Irido-Corneal Angle of the Eye," issued as U.S. Pat. No. 10,821,023; and U.S. patent application Ser. No. 16/125,588, filed Sep. 7, 2018, for "Non-Invasive and Minimally Invasive Laser Surgery for the Reduction of Intraocular Pressure in the Eye," the entire disclosures of which are incorporated herein by reference.

TECHNICAL FIELD

The present disclosure relates generally to the field of medical devices and treatment of diseases in ophthalmology including glaucoma, and more particularly to systems, apparatuses, and methods for treating the trabecular meshwork and Schlemm's canal using a femtosecond laser.

BACKGROUND

Before describing the different types of glaucoma and current diagnosis and treatments options, a brief overview of the anatomy of the eye is provided.

Anatomy of the Eye

With reference to FIGS. 1-3, the outer tissue layer of the eye 1 includes a sclera 2 that provides the structure of the eye's shape. In front of the sclera 2 is a cornea 3 that is comprised of transparent layers of tissue that allow light to enter the interior of the eye. Inside the eye 1 is a crystalline lens 4 that is connected to the eye by fiber zonules 5, which are connected to the ciliary body 6. Between the crystalline lens 4 and the cornea 3 is an anterior chamber 7 that contains a flowing clear liquid called aqueous humor 8. Encircling the perimeter of the crystalline lens 4 is an iris 9 which forms a pupil around the approximate center of the crystalline lens. A posterior chamber 23 is an annular volume behind the iris 9 and bounded by the ciliary body 6, fiber zonules 5, and the crystalline lens 4. The vitreous humor 10 is located between the crystalline lens 4 and the retina 11. Light entering the eye is optically focused through the cornea 3 and crystalline lens.

With reference to FIG. 2, the corneoscleral junction of the eye is the portion of the anterior chamber 7 at the intersection of the iris 9, the sclera 2, and the cornea 3. The anatomy of the eye 1 at the corneoscleral junction includes a trabecular meshwork 12. The trabecular meshwork 12 is a fibrous network of tissue that encircles the iris 9 within the eye 1. In simplified, general terms the tissues of the corneoscleral junction are arranged as follows: the iris 9 meets the ciliary body 6, the ciliary body meets with the underside of the scleral spur 14, the top of the scleral spur serves as an attachment point for the bottom of the trabecular meshwork 12. The ciliary body is present mainly in the posterior chamber, but also extends into the very corner of the anterior chamber 7. The network of tissue layers that make up the trabecular meshwork 12 are porous and thus present a pathway for the egress of aqueous humor 8 flowing from the anterior chamber 7. This pathway may be referred to herein as an aqueous humor outflow pathway, an aqueous outflow pathway, or simply an outflow pathway.

Referring to FIG. 3, the pathway formed by the pores in the trabecular meshwork 12 connect to a set of thin porous tissue layers called the uveal 15, the corneoscleral meshwork 16, and the juxtacanalicular tissue 17. The juxtacanalicular tissue 17, in turn, abuts a structure called Schlemm's canal 18. The Schlemm's canal 18 carries a mixture of aqueous humor 8 and blood from the surrounding tissue to drain into the venous system though a system of collector channels 19. As shown in FIG. 2, the vascular layer of the eye, referred to as the choroid 20, is next to the sclera 2. A space, called the suprachoroidal space 21, may be present between the choroid 20 and the sclera 2. The general region near the periphery of the wedge between the cornea 3 and the iris 9, running circumferentially is called the irido-corneal angle 13. The irido-corneal angle 13 may also be referred to as the corneal angle of the eye or simply the angle of the eye. The ocular tissues illustrated in FIG. 3 are all considered to be within the irido-corneal angle 13.

With reference to FIG. 4, two possible outflow pathways for the movement of aqueous humor 8 include a trabecular outflow pathway 40 and a uveoscleral outflow pathway 42. Aqueous humor 8, which is produced by the ciliary body 6, flows from the posterior chamber 23 through the pupil into the anterior chamber 7, and then exits the eye through one or more of the two different outflow pathways 40, 42. Approximately 90% of the aqueous humor 8 leaves via the trabecular outflow pathway 40 by passing through the trabecular meshwork 12, into the Schlemm's canal 18 and through one or more plexus of collector channels 19 before draining through a drain path 41 into the venous system. Any remaining aqueous humor 8 leaves primarily through the uveoscleral outflow pathway 42. The uveoscleral outflow pathway 42 passes through the ciliary body 6 face and iris root into the suprachoroidal space 21 (shown in FIG. 2). Aqueous humor 8 drains from the suprachoroidal space 21, from which it can be drained through the sclera 2.

The intra-ocular pressure of the eye depends on the aqueous humor 8 outflow through the trabecular outflow pathway 40 and the resistance to outflow of aqueous humor through the trabecular outflow pathway. The intra-ocular pressure of the eye is largely independent of the aqueous humor 8 outflow through the uveoscleral outflow pathway 42. Resistance to the outflow of aqueous humor 8 through the trabecular outflow pathway 40 may lead to elevated intra-ocular pressure of the eye, which is a widely recognized risk factor for glaucoma. Resistance through the trabecular outflow pathway 40 may increase due a collapsed or malfunctioning Schlemm's canal 18 and trabecular meshwork 12.

Referring to FIG. 5, as an optical system, the eye 1 is represented by an optical model described by idealized centered and rotationally symmetrical surfaces, entrance and exit pupils, and six cardinal points: object and image space focal points, first and second principal planes, and first and second nodal points. Angular directions relative to the human eye are often defined with respect to an optical axis 24, a visual axis 26, a pupillary axis 28 and a line of sight 29 of the eye. The optical axis 24 is the symmetry axis, the line connecting the vertices of the idealized surfaces of the eye. The visual axis 26 connects the foveal center 22 with the first and second nodal points to the object. The line of sight 29 connects the fovea through the exit and entrance pupils to the object. The pupillary axis 28 is normal to the anterior surface of the cornea 3 and directed to the center of the entrance pupil. These axes of the eye differ from one another only by a few degrees and fall within a range of what is generally referred to as the direction of view.

Glaucoma

Glaucoma is a group of diseases that can harm the optic nerve and cause vision loss or blindness. It is the leading cause of irreversible blindness. Approximately 80 million people are estimated to have glaucoma worldwide and of these, approximately 6.7 million are bilaterally blind. More than 2.7 million Americans over age 40 have glaucoma. Symptoms start with loss of peripheral vision and can progress to blindness.

There are two forms of glaucoma, one is referred to as closed-angle glaucoma, the other as open-angled glaucoma. With reference to FIGS. 1-4, in closed-angle glaucoma, the iris 9 in a collapsed anterior chamber 7 may obstruct and close off the flow of aqueous humor 8. In open-angle glaucoma, which is the more common form of glaucoma, the permeability of ocular tissue may be affected by irregularities in the juxtacanalicular tissue 17 and inner wall of Schlemm's canal 18a, blockage of tissue in the irido-corneal angle 13 along the trabecular outflow pathway 40.

As previously stated, elevated intra-ocular pressure (IOP) of the eye, which damages the optic nerve, is a widely recognized risk factor for glaucoma. However, not every person with increased eye pressure will develop glaucoma, and glaucoma can develop without increased eye pressure. Nonetheless, it is desirable to reduce elevated IOP of the eye to reduce the risk of glaucoma.

Methods of diagnosing conditions of the eye of a patient with glaucoma include visual acuity tests and visual field tests, dilated eye exams, tonometry, i.e. measuring the intra-ocular pressure of the eye, and pachymetry, i.e. measuring the thickness of the cornea. Deterioration of vision starts with the narrowing of the visual field and progresses to total blindness. Imaging methods include slit lamp examination, observation of the irido-corneal angle with a gonioscopic lens and optical coherence tomography (OCT) imaging of the anterior chamber and the retina Once diagnosed, some clinically proven treatments are available to control or lower the intra-ocular pressure of the eye to slow or stop the progress of glaucoma. The most common treatments include: 1) medications, such as eye drops or pills, 2) laser surgery, and 3) traditional surgery. Treatment usually begins with medication. However, the efficacy of medication is often hindered by patient non-compliance. When medication does not work for a patient, laser surgery is typically the next treatment to be tried. Traditional surgery is invasive, more high risk than medication and laser surgery, and has a limited time window of effectiveness. Traditional surgery is thus usually reserved as a last option for patients whose eye pressure cannot be controlled with medication or laser surgery.

Laser Surgery

With reference to FIG. 2, laser surgery for glaucoma targets the trabecular meshwork 12 to decrease aqueous humor 8 flow resistance. Common laser treatments include Argon Laser Trabeculoplasty (ALT), Selective Laser Trabeculoplasty (SLT) and Excimer Laser Trabeculostomy (ELT).

ALT was the first laser trabeculoplasty procedure. During the procedure, an argon laser of 514 nm wavelength is applied to the trabecular meshwork 12 around 180 degrees of the circumference of the irido-corneal angle 13. The argon laser induces a thermal interaction with the ocular tissue that produces openings in the trabecular meshwork 12. ALT, however, causes scarring of the ocular tissue, followed by inflammatory responses and tissue healing that may ultimately close the opening through the trabecular meshwork 12 formed by the ALT treatment, thus reducing the efficacy of the treatment. Furthermore, because of this scarring, ALT therapy is typically not repeatable.

SLT is designed to lower the scarring effect by selectively targeting pigments in the trabecular meshwork 12 and reducing the amount of heat delivered to surrounding ocular tissue. During the procedure, a solid-state laser of 532 nm wavelength is applied to the trabecular meshwork 12 between 180 to 360 degrees around the circumference of the irido-corneal angle 13 to remove the pigmented cells lining the trabeculae which comprise the trabecular meshwork. The collagen ultrastructure of the trabecular meshwork is preserved during SLT. 12. SLT treatment can be repeated, but subsequent treatments have lower effects on IOP reduction.

ELT uses a 308 nm wavelength ultraviolet (UV) excimer laser and non-thermal interaction with ocular tissue to treat the trabecular meshwork 12 and inner wall of Schlemm's canal in a manner that does not invoke a healing response. Therefore, the IOP lowering effect lasts longer. However, because the UV light of the laser cannot penetrate deep into the eye, the laser light is delivered to the trabecular meshwork 12 via an optical fiber inserted into the eye 1 through an opening and the fiber is brought into contact with the trabecular meshwork. The procedure is highly invasive and is generally practiced simultaneously with cataract procedures when the eye is already surgically open. Like ALT and SLT, ELT also lacks control over the amount of IOP reduction.

None of these existing laser treatments represents an ideal treatment for glaucoma. Accordingly, what is needed are systems, apparatuses, and method for laser surgery treatment of glaucoma that effectively reduce IOP non-invasively without significant scarring of tissue, so the treatment may be completed in a single procedure and repeated at a later time if necessary.

SUMMARY

The present disclosure relates to a method of treating a target volume of ocular tissue of an irido-corneal angle of an eye with a laser having a direction of propagation toward the target volume of ocular tissue, where the target volume of ocular tissue is characterized by a distal extent, a proximal extent, and a lateral extent. The method includes initially photodisrupting tissue at an initial depth corresponding to the distal extent of the target volume of ocular tissue. To this end, light from a femtosecond laser is focused at a spot in the tissue at the initial depth. Optical energy sufficient to photodisrupt the tissue is then applied to the tissue by, for example, scanning the laser in multiple directions defining an initial treatment plane, to thereby photodisrupt an initial layer of tissue of the target volume.

The method also includes subsequently photodisrupting tissue at one or more subsequent depths between the distal extent of the target volume of ocular tissue and the proximal extent of the target volume by moving a focus of the laser in a direction opposite the direction of propagation of the laser. To this end, light from a femtosecond laser is focused at a spot in the tissue at a subsequent depth. Optical energy sufficient to photodisrupt the tissue is then applied to the tissue by, for example, scanning the laser in multiple directions defining a subsequent treatment plane, to thereby photodisrupt a subsequent layer of tissue of the target volume. Photodisrupting at one or more subsequent depths is repeated at a plurality of different subsequent depths until tissue at the proximal extent of the target volume of ocular tissue is photodisrupted.

In additional aspects, the method includes, after photodisrupting the target volume of tissue, photodisrupting tissue debris or bubbles between the proximal extent of the target volume of ocular tissue and the distal extent of the target volume by moving the focus of the laser in the direction of propagation of the laser and rescanning the laser at one or more of the subsequent treatment planes and the initial treatment plane. The method may further include, repeating the initial photodisrupting of tissue and the subsequent photodisrupting of tissue one or more times.

The present disclosure also relates to a system for treating a target volume of ocular tissue of an irido-corneal angle of an eye with a laser, where the target volume of ocular tissue characterized by a distal extent, a proximal extent, and a lateral extent. The system includes a first optical subsystem including a focusing objective configured to be coupled to the eye, and a second optical subsystem including a laser source configured to output a laser beam. The second optical subsystem also includes a plurality of components configured to one or more of focus, scan, and direct the laser beam through the focusing objective, in a direction of propagation toward the target volume of ocular tissue.

The system further includes a control system coupled to the second optical subsystem and configured to control the focus and scan of the laser beam to initially photodisrupt tissue at an initial depth corresponding to the distal extent of the target volume of ocular tissue. To this end, the control system is configured to focus light from a femtosecond laser at a spot in the tissue at the initial depth, and then apply optical energy to the tissue, where the energy is sufficient to photodisrupt tissue. The control system controls the focus and scan of the laser beam during application of optical energy by being further configured to scan the laser in multiple directions defining an initial treatment plane, to thereby photodisrupt an initial layer of tissue of the target volume of ocular tissue.

The control system is also configured to control the focus and scan of the laser beam to subsequently photodisrupt tissue at one or more subsequent depths between the distal extent of the target volume of ocular tissue and the proximal extent of the target volume by moving a focus of the laser in a direction opposite the direction of propagation of the laser. To this end, the control system is configured to focus light from a femtosecond laser at a spot in the tissue at a subsequent depth, and then apply optical energy to the tissue, where the energy is sufficient to photodisrupt tissue. The control system controls the focus and scan of the laser beam during application of optical energy by being further configured to scan the laser in multiple directions defining a subsequent treatment plane, to thereby photodisrupt a subsequent layer of tissue of the target volume of ocular tissue.

In additional aspects, the control system is configured to control the focus and scan of the laser beam to photodisrupt tissue debris or bubbles between the proximal extent of the target volume of ocular tissue and the distal extent of the target volume of ocular tissue by moving the focus of the laser in the direction of propagation of the laser, after photodisrupting the target volume of ocular tissue, and rescanning the laser at one or more of the subsequent treatment planes and the initial treatment plane. The control system is further configured to control the focus and scan of the laser beam to repeat the initial photodisrupting of tissue and the subsequent photodisrupting of tissue one or more times.

The present disclosure also relates to a method of treating an eye comprising an anterior chamber, a Schlemm's canal, and a trabecular meshwork therebetween. The method includes initially photodisrupting ocular tissue at or near an interface of an inner wall of the Schlemm's canal and the trabecular meshwork. To this end, light from a femtosecond laser is focused at a spot in the ocular tissue at or near the interface of the inner wall of the Schlemm's canal and the trabecular meshwork. Optical energy sufficient to photodisrupt the tissue is then applied to the tissue. The method also includes subsequently photodisrupting ocular tissue of the trabecular meshwork. To this end, light from a femtosecond laser is focused at a spot in tissue of the trabecular meshwork. Optical energy sufficient to photodisrupt the tissue is then applied to the tissue. In additional aspects, the method includes, repeating the initial photodisrupting of ocular tissue and the subsequent photodisrupting of ocular tissue one or more times until an opening is formed between the anterior chamber and the Schlemm's canal.

The present disclosure also relates to a system for treating an eye comprising an anterior chamber, a Schlemm's canal, and a trabecular meshwork therebetween. The system includes a first optical subsystem including a focusing objective configured to be coupled to the eye, and a second optical subsystem including a laser source configured to output a laser beam. The second optical subsystem further includes a plurality of components configured to one or more of focus, scan, and direct the laser beam through the focusing objective, toward ocular tissue.

The system also includes a control system coupled to the second optical subsystem and configured to control the focus and the scan of the laser beam to initially photodisrupt ocular tissue at or near an interface of an inner wall of the Schlemm's canal and the trabecular meshwork. To this end, the control system is configured to focus light from a femtosecond laser at a spot in the ocular tissue at or near the interface of the inner wall of the Schlemm's canal and the trabecular meshwork, and then apply optical to the tissue, where the energy is sufficient to photodisrupt tissue. The control system is also configured to control the focus and scan of the laser beam to subsequently photodisrupt tissue of the trabecular meshwork. To this end, the control system is configured to focus light from a femtosecond laser at a spot in tissue of the trabecular meshwork, and then apply optical energy to the tissue, where the energy is sufficient to photodisrupt tissue. In additional aspects, the control system is further configured to control the focus and scan of the laser beam to repeat the initial photodisrupting of ocular tissue and the subsequent photodisrupting of ocular tissue one or more times until an opening is formed between the anterior chamber and the Schlemm's canal.

It is understood that other aspects of apparatuses and methods will become apparent to those skilled in the art from the following detailed description, wherein various aspects of apparatuses and methods are shown and described by way of illustration. As will be realized, these aspects may be implemented in other and different forms and its several details are capable of modification in various other respects. Accordingly, the drawings and detailed description are to be regarded as illustrative in nature and not as restrictive.

BRIEF DESCRIPTION OF THE DRAWINGS

Various aspects of systems, apparatuses, and methods will now be presented in the detailed description by way of example, and not by way of limitation, with reference to the accompanying drawings, wherein.

DETAILED DESCRIPTION

Disclosed herein are systems, apparatuses, and methods for safely and effectively reducing intra-ocular pressure (IOP) in the eye to either treat or reduce the risk of glaucoma. The systems, apparatuses, and methods enable access to the irido-corneal angle of the eye and integrate laser surgery techniques with high resolution imaging to precisely diagnose, locate, and treat abnormal ocular tissue conditions within the irido-corneal angle that may be causing elevated IOP.

An integrated surgical system disclosed herein is configured to reduce intraocular pressure in an eye having a cornea, an anterior chamber, and an irido-corneal angle comprising an aqueous humor outflow pathway formed of a trabecular meshwork, a Schlemm's canal, and one or more collector channels branching from the Schlemm's canal. The integrated surgical system also includes a first optical subsystem and a second optical subsystem. The first optical subsystem includes a window configured to be coupled to the cornea and an exit lens configured to be coupled to the window. The second optical subsystem includes an optical coherence tomography (OCT) imaging apparatus configured to output an OCT beam, a laser source configured to output a laser beam, and a plurality of components, e.g., lenses and mirrors, configured to condition, combine, or direct the OCT beam and the laser beam toward the first optical subsystem.

The integrated surgical system also includes a control system coupled to the OCT imaging apparatus, the laser source, and the second optical subsystem. The controller is configured to instruct the OCT imaging apparatus to output an OCT beam and the laser source to output a laser beam, for delivery through the cornea, and the anterior chamber into the irido-corneal angle. In one configuration, the control system controls the second optical subsystem, so the OCT beam and the laser beam are directed into the first optical subsystem along a second optical axis that is offset from the first optical axis and that extends into the irido-corneal angle along an angled beam path 30.

Figure 2:
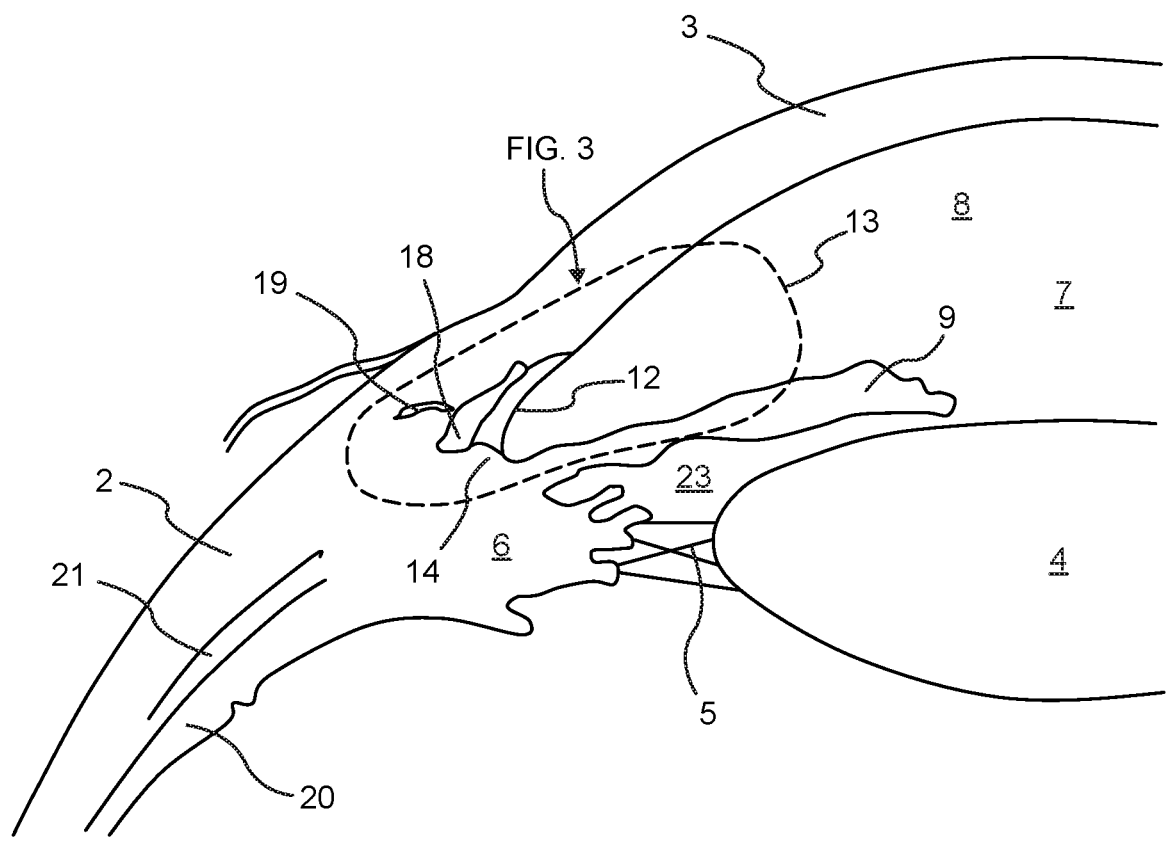
FIG. 2 is a sectional schematic illustration of the irido-corneal angle of the eye of FIG. 1.
Figure 3:
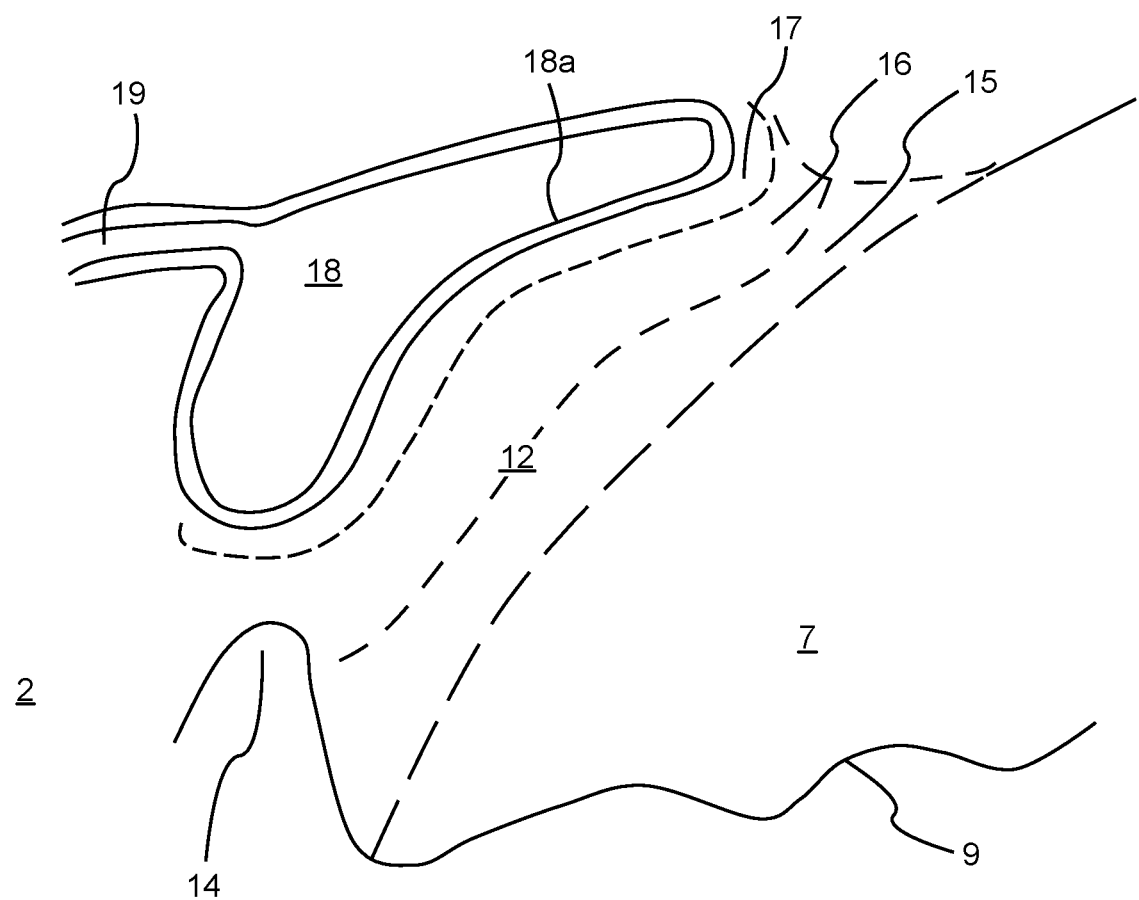
FIG. 3 is a sectional schematic illustration detailing anatomical structures in the irido-corneal angle of FIG. 2, including the trabecular meshwork, Schlemm's canal, and one or more collector channels branching from the Schlemm's canal.
Figure 4:
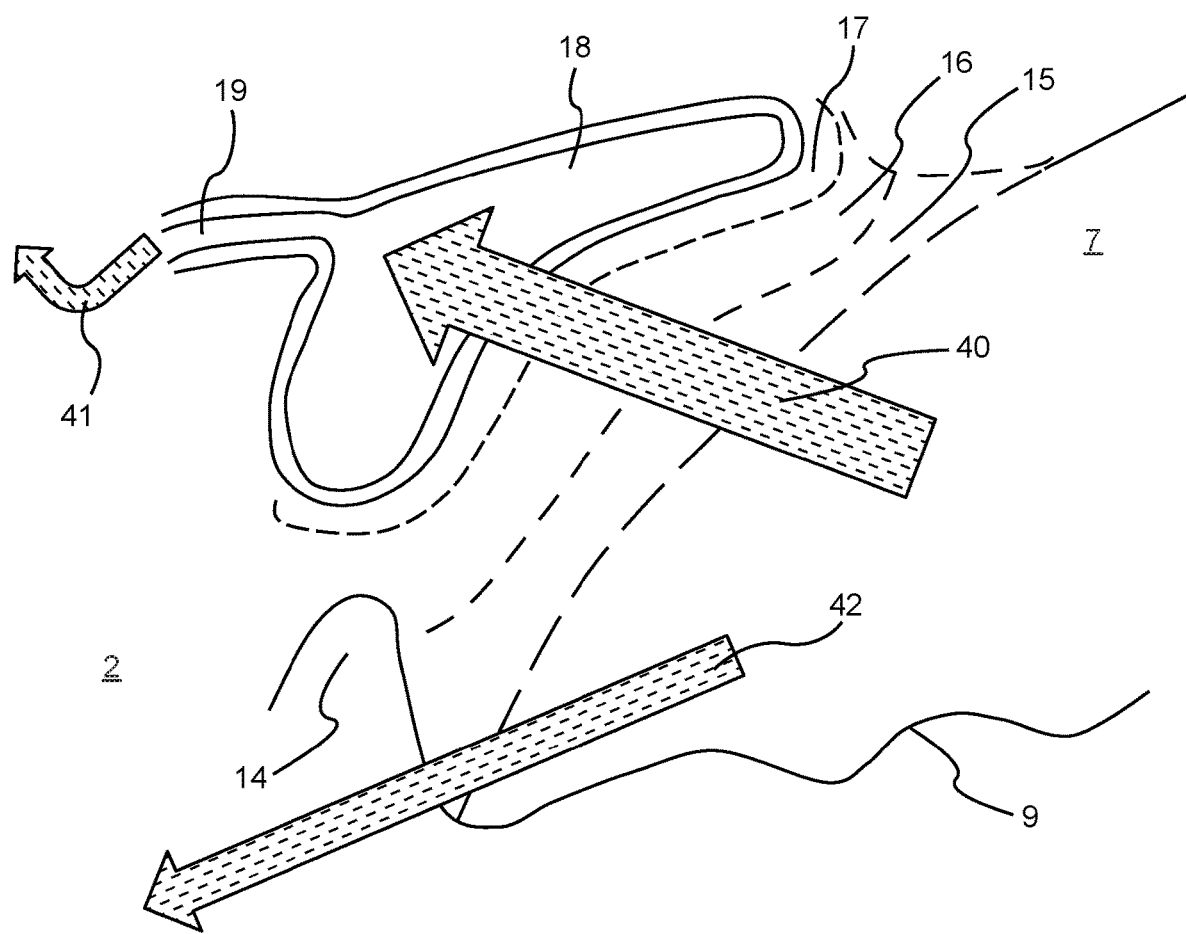
FIG. 4 is a sectional schematic illustration of various outflow pathways for aqueous humor through the trabecular meshwork, Schlemm's canal, and collector channels of FIG. 3.
Figure 5:
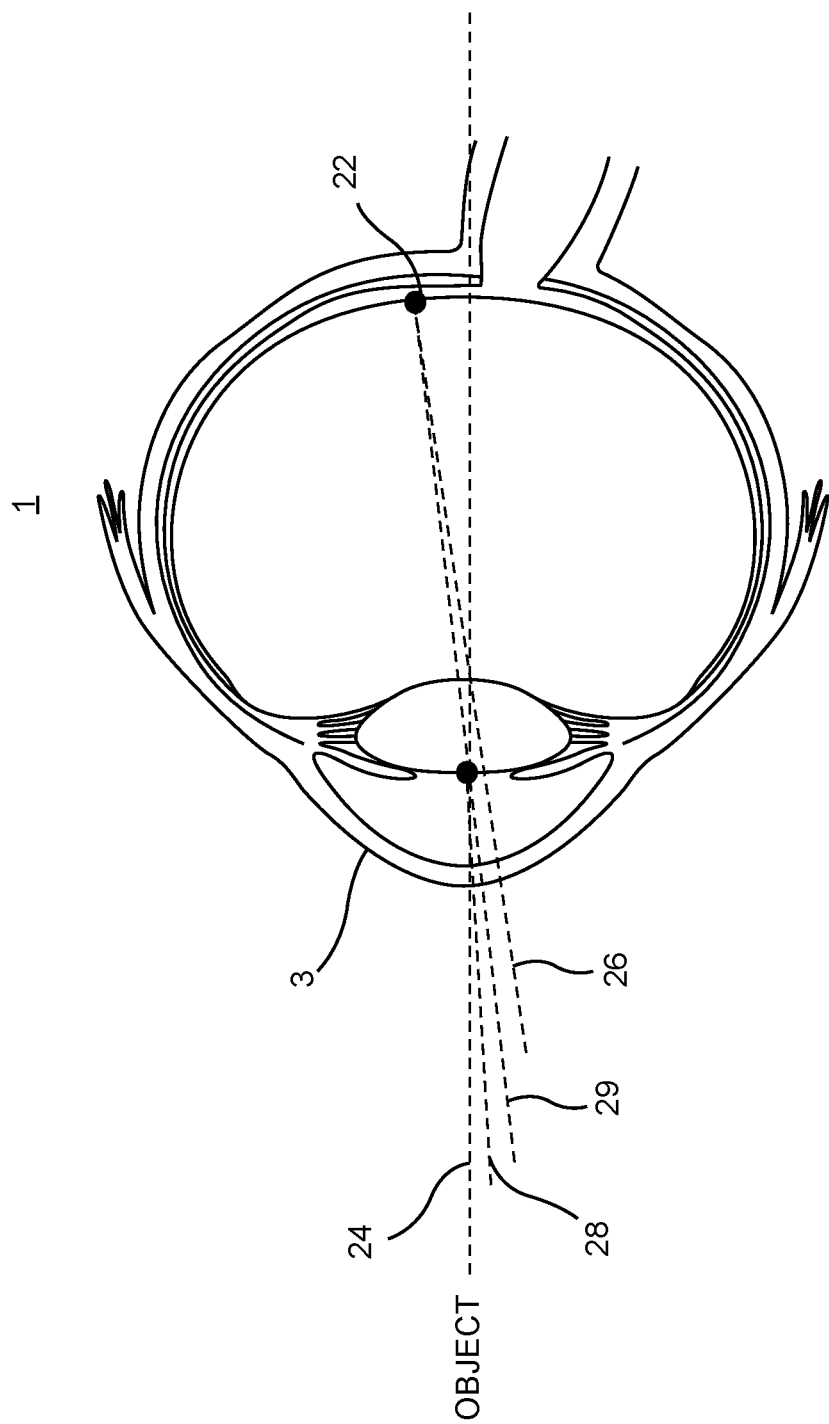
FIG. 5 is a sectional schematic illustration of a human eye showing various axes associated with the eye.

Directing each of an OCT beam and a laser beam along the same second optical axis into the irido-corneal angle of the eye is beneficial in that it enables direct application of the result of the evaluation of the condition into the treatment plan and surgery with precision in one clinical setting. Furthermore, combining OCT imaging and laser treatment allows targeting the ocular tissue with precision not available with any existing surgical systems and methods. Surgical precision afforded by the integrated surgical system allows for the affecting of only the targeted tissue of microscopic size and leaves the surrounding tissue intact. The microscopic size scale of the affected ocular tissue to be treated in the irido-corneal angle of the eye ranges from a few micrometers to a few hundred micrometers. For example, with reference to FIGS. 2 and 3, the cross-sectional size of the normal Schlemm's canal 18 is an oval shape of a few tens of micrometers by a few hundred micrometers. The diameter of collector channels 19 and veins is a few tens of micrometers. The thickness of the juxtacanalicular tissue 17 is a few micrometers, the thickness of the trabecular meshwork 12 is around a hundred micrometers.

The control system of the integrated surgical system is further configured to instruct the laser source to modify a volume of ocular tissue within the outflow pathway to reduce a pathway resistance present in one or more of the trabecular meshwork, the Schlemm's canal, and the one or more collector channels by applying the laser beam to ocular tissue defining the volume to thereby cause photo-disruptive interaction with the ocular tissue to reduce the pathway resistance or create a new outflow pathway.

The laser source may be a femtosecond laser. Femtosecond lasers provide non-thermal photo-disruption interaction with ocular tissue to avoid thermal damage to surrounding tissue. Further, unlike other surgical methods, with femtosecond laser treatment opening surface incisions penetrating the eye can be avoided, enabling a non-invasive treatment. Instead of performing the treatment in a sterile surgical room, the non-invasive treatment can be performed in a non-sterile outpatient facility.

An additional imaging component may be included the integrated surgical system to provide direct visual observation of the irido-corneal angle along an angle of visual observation. For example, a microscope or imaging camera may be included to assist the surgeon in the process of docking the eye to the patient interface or an immobilizing device, location of ocular tissues in the eye and observing the progress of the surgery. The angle of visual observation can also be along the angled beam path 30 to the irido-corneal angle 13 through the cornea 3 and the anterior chamber 7.

Images from the OCT imaging apparatus and the additional imaging component providing visual observation, e.g. microscope, are combined on a display device such as a computer monitor. Different images can be registered and overlaid on a single window, enhanced, processed, differentiated by false color for easier understanding. Certain features are computationally recognized by a computer processor, image recognition and segmentation algorithm can be enhanced, highlighted, marked for display. The geometry of the treatment plan can also be combined and registered with imaging information on the display device and marked up with geometrical, numerical and textual information. The same display can also be used for user input of numerical, textual and geometrical nature for selecting, highlighting and marking features, inputting location information for surgical targeting by keyboard, mouse, cursor, touchscreen, audio or other user interface devices.

OCT Imaging

Figure 1:
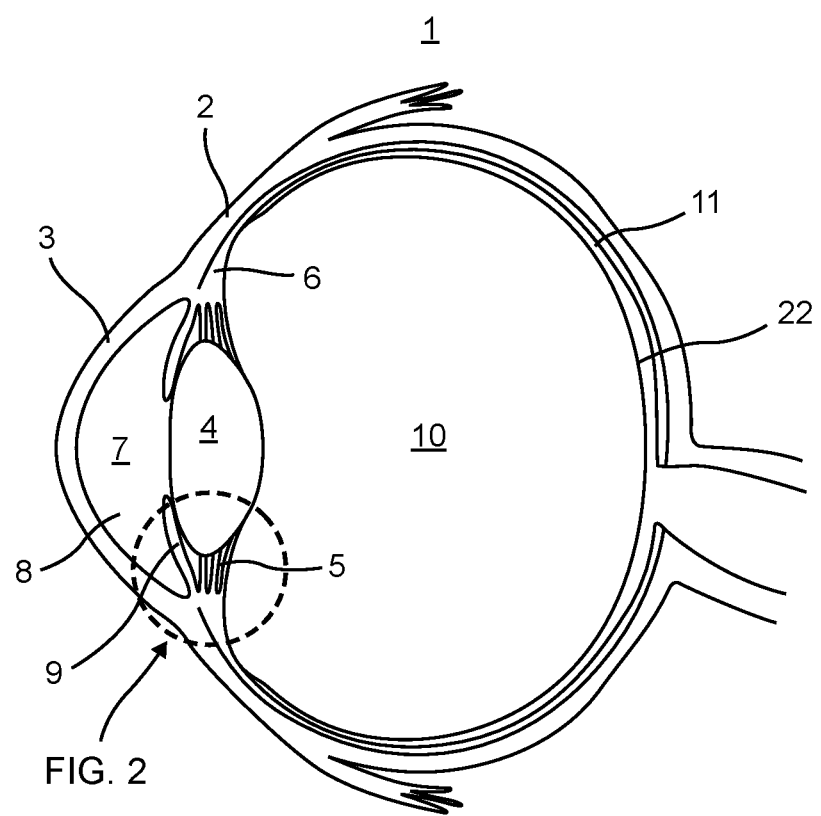
FIG. 1 is a sectional schematic illustration of a human eye and its interior anatomical structures.

The main imaging component of the integrated surgical system disclosed herein is an OCT imaging apparatus. OCT technology may be used to diagnose, locate and guide laser surgery directed to the irido-corneal angle of the eye. For example, with reference to FIGS. 1-3, OCT imaging may be used to determine the structural and geometrical conditions of the anterior chamber 7, to assess possible obstruction of the trabecular outflow pathway 40 and to determine the accessibility of the ocular tissue for treatment. As previously described, the iris 9 in a collapsed anterior chamber 7 may obstruct and close off the flow of aqueous humor 8, resulting in closed-angle glaucoma. In open-angle glaucoma, where the macroscopic geometry of the angle is normal, the permeability of ocular tissue may be affected, by blockage of tissue along the trabecular outflow pathway 40 or by the collapse of the Schlemm's canal 18 or collector channels 19.

OCT imaging can provide the necessary spatial resolution, tissue penetration and contrast to resolve microscopic details of ocular tissue. When scanned, OCT imaging can provide two-dimensional (2D) cross-sectional images of the ocular tissue. As another aspect of the integrated surgical system, 2D cross-sectional images may be processed and analyzed to determine the size, shape and location of structures in the eye for surgical targeting. It is also possible to reconstruct three-dimensional (3D) images from a multitude of 2D cross-sectional images but often it is not necessary. Acquiring, analyzing and displaying 2D images is faster and can still provide all information necessary for precise surgical targeting.

OCT is an imaging modality capable of providing high resolution images of materials and tissue. Imaging is based on reconstructing spatial information of the sample from spectral information of scattered light from within the sample. Spectral information is extracted by using an interferometric method to compare the spectrum of light entering the sample with the spectrum of light scattered from the sample. Spectral information along the direction that light is propagating within the sample is then converted to spatial information along the same axis via the Fourier transform. Information lateral to the OCT beam propagation is usually collected by scanning the beam laterally and repeated axial probing during the scan. 2D and 3D images of the samples can be acquired this way. Image acquisition is faster when the interferometer is not mechanically scanned in a time domain OCT, but interference from a broad spectrum of light is recorded simultaneously, this implementation is called a spectral domain OCT. Faster image acquisition may also be obtained by scanning the wavelength of light rapidly from a wavelength scanning laser in an arrangement called a swept-source OCT.

The axial spatial resolution limit of the OCT is inversely proportional to the bandwidth of the probing light used. Both spectral domain and swept source OCTs are capable of axial spatial resolution below 5 micrometers (pa) with sufficiently broad bandwidth of 100 nanometers (nm) or more. In the spectral domain OCT, the spectral interference pattern is recorded simultaneously on a multichannel detector, such as a charge coupled device (CCD) or complementary metal oxide semiconductor (CMOS) camera, while in the swept source OCT the interference pattern is recorded in sequential time steps with a fast optical detector and electronic digitizer. There is some acquisition speed advantage of the swept source OCT but both types of systems are evolving and improving rapidly, and resolution and speed is sufficient for purposes of the integrated surgical system disclosed herein. Stand-alone OCT systems and OEM components are now commercially available from multiple vendors, such as Optovue Inc., Fremont, Calif., Topcon Medical Systems, Oakland, N.J., Carl Zeiss Meditec AG, Germany, Nidek, Aichi, Japan, Thorlabs, Newton, N.J., Santec, Aichi, Japan, Axsun, Billercia, Mass., and other vendors.

Femtosecond Laser Source

The preferred surgical component of the integrated surgical system disclosed herein is a femtosecond laser. A femtosecond laser provides highly localized, non-thermal photo-disruptive laser-tissue interaction with minimal collateral damage to surrounding ocular tissue. Photo-disruptive interaction of the laser is utilized in optically transparent tissue. The principal mechanism of laser energy deposition into the ocular tissue is not by absorption but by a highly nonlinear multiphoton process. This process is effective only at the focus of the pulsed laser where the peak intensity is high. Regions where the beam is traversed but not at the focus are not affected by the laser. Therefore, the interaction region with the ocular tissue is highly localized both transversally and axially along the laser beam. The process can also be used in weakly absorbing or weakly scattering tissue. While femtosecond lasers with photo-disruptive interactions have been successfully used in ophthalmic surgical systems and commercialized in other ophthalmic laser procedures, none have been used in an integrated surgical system that accesses the irido-corneal angle.

In known refractive procedures, femtosecond lasers are used to create corneal flaps, pockets, tunnels, arcuate incisions, lenticule shaped incisions, partial or fully penetrating corneal incisions for keratoplasty. For cataract procedures the laser creates a circular cut on the capsular bag of the eye for capsulotomy and incisions of various patterns in the lens for braking up the interior of the crystalline lens to smaller fragments to facilitate extraction. Entry incisions through the cornea opens the eye for access with manual surgical devices and for insertions of phacoemulsification devices and intra-ocular lens insertion devices. Several companies have commercialized such surgical systems, among them the IntraLase system now available from Johnson & Johnson Vision, Santa Ana, Calif., The LenSx and WaveLight systems from Alcon, Fort Worth, Tex., other surgical systems from Bausch and Lomb, Rochester, N.Y., Carl Zeiss Meditec AG, Germany, Ziemer, Port, Switzerland, and LENSAR, Orlando, Fla.

These existing systems are developed for their specific applications, for surgery in the cornea, and the crystalline lens and its capsular bag and are not capable of performing surgery in the irido-corneal angle 13 for several reasons. First, the irido-corneal angle 13 is not accessible with these surgical laser systems because the irido-corneal angle is too far out in the periphery and is outside of surgical range of these systems. Second, the angle of the laser beam from these systems, which is along the optical axis 24 to the eye 1, is not appropriate to reaching the irido-corneal angle 13, where there is significant scattering and optical distortion at the applied wavelength. Third, any imaging capabilities these systems may have do not have the accessibility, penetration depth and resolution to image the tissue along the trabecular outflow pathway 40 with sufficient detail and contrast.

In accordance with the integrated surgical system disclosed herein, clear access to the irido-corneal angle 13 is provided along the angled beam path 30. The tissue, e.g., cornea 3 and the aqueous humor 8 in the anterior chamber 7, along this angled beam path 30 is transparent for wavelengths from approximately 400 nm to 2500 nm and femtosecond lasers operating in this region can be used. Such mode locked lasers work at their fundamental wavelength with Titanium, Neodymium or Ytterbium active material. Non-linear frequency conversion techniques known in the art, frequency doubling, tripling, sum and difference frequency mixing techniques, optical parametric conversion can convert the fundamental wavelength of these lasers to practically any wavelength in the above mentioned transparent wavelength range of the cornea.

Existing ophthalmic surgical systems apply lasers with pulse durations longer than 1 ns have higher photo-disruption threshold energy, require higher pulse energy and the dimension of the photo-disruptive interaction region is larger, resulting in loss of precision of the surgical treatment. When treating the irido-corneal angle 13, however, higher surgical precision is required. To this end, the integrated surgical system may be configured to apply lasers with pulse durations from 10 femtosecond (fs) to 1 nanosecond (ns) for generating photo-disruptive interaction of the laser beam with ocular tissue in the irido-corneal angle 13. While lasers with pulse durations shorter than 10 fs are available, such laser sources are more complex and more expensive. Lasers with the described desirable characteristics, e.g., pulse durations from 10 femtosecond (fs) to 1 nanosecond (ns), are commercially available from multiple vendors, such as Newport, Irvine, Calif., Coherent, Santa Clara, Calif., Amplitude Systems, Pessac, France, NKT Photonics, Birkerod, Denmark, and other vendors.

Accessing the Irido-Corneal Angle

Figure 6:
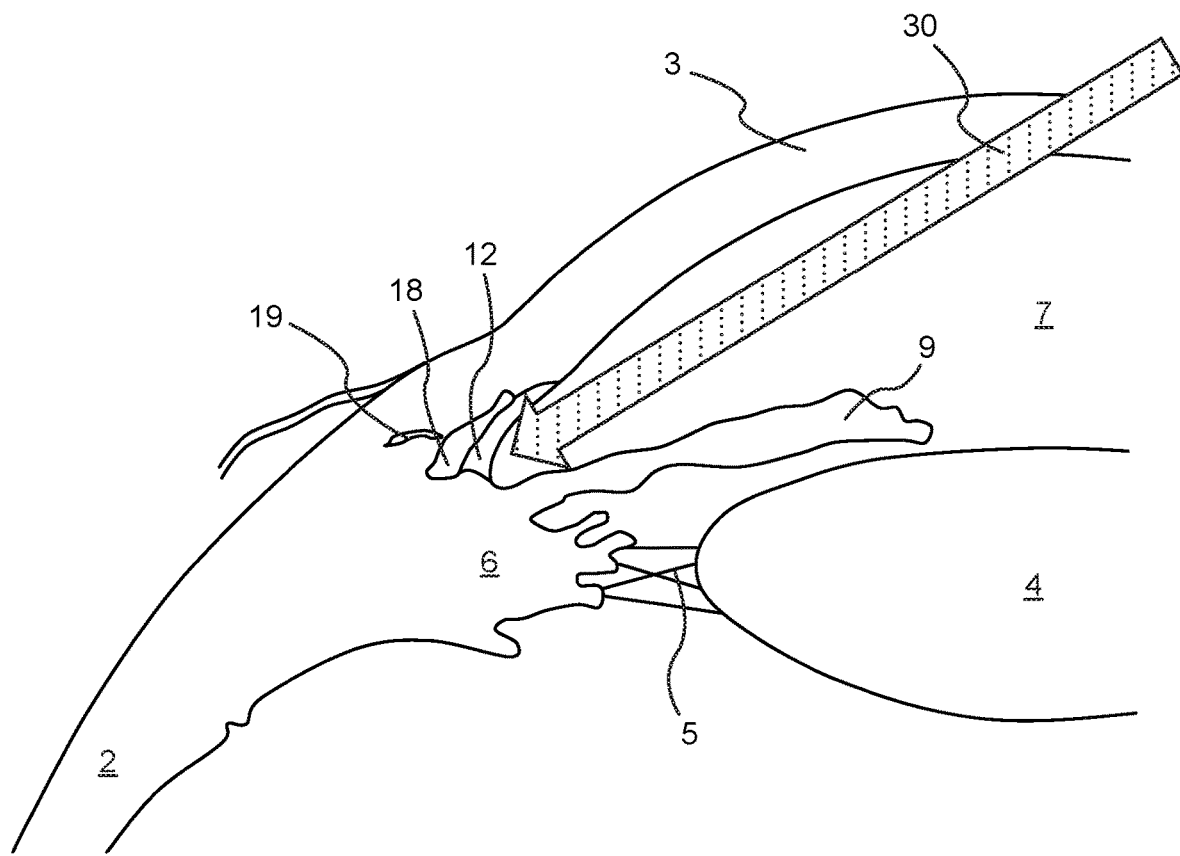
FIG. 6 is a sectional schematic illustration of an angled beam path along which one or more light beams may access the irido-corneal angle of the eye.

An important feature afforded by the integrated surgical system is access to the targeted ocular tissue in the irido-corneal angle 13. With reference to FIG. 6, the irido-corneal angle 13 of the eye may be accessed via the integrated surgical system along an angled beam path 30 passing through the cornea 3 and through the aqueous humor 8 in the anterior chamber 7. For example, one or more of an imaging beam, e.g., an OCT beam and/or a visual observation beam, and a laser beam may access the irido-corneal angle 13 of the eye along the angled beam path 30.

An optical system disclosed herein is configured to direct a light beam to an irido-corneal angle 13 of an eye along an angled beam path 30. The optical system includes a first optical subsystem and a second optical subsystem. The first optical subsystem includes a window formed of a material with a refractive index $n_w$ and has opposed concave and convex surfaces. The first optical subsystem also includes an exit lens formed of a material having a refractive index $n_x$. The exit lens also has opposed concave and convex surfaces. The concave surface of the exit lens is configured to couple to the convex surface of the window to define a first optical axis extending through the window and the exit lens. The concave surface of the window is configured to detachably couple to a cornea of the eye with a refractive index $n_c$ such that, when coupled to the eye, the first optical axis is generally aligned with the direction of view of the eye.

The second optical subsystem is configured to output a light beam, e.g., an OCT beam or a laser beam. The optical system is configured so that the light beam is directed to be incident at the convex surface of the exit lens along a second optical axis at an angle $\alpha$ that is offset from the first optical axis. The respective geometries and respective refractive indices $n_x$, and $n_w$ of the exit lens and window are configured to compensate for refraction and distortion of the light beam by bending the light beam so that it is directed through the cornea 3 of the eye toward the irido-corneal angle 13. More specifically, the first optical system bends the light beam to that the light beam exits the first optical subsystem and enters the cornea 3 at an appropriate angle so that the light beam progresses through the cornea and the aqueous humor 8 in a direction along the angled beam path 30 toward the irido-corneal angle 13.

Accessing the irido-corneal angle 13 along the angled beam path 30 provides several advantages. An advantage of this angled beam path 30 to the irido-corneal angle 13 is that the OCT beam and laser beam passes through mostly clear tissue, e.g., the cornea 3 and the aqueous humor 8 in the anterior chamber 7. Thus, scattering of these beams by tissue is not significant. With respect to OCT imaging, this enables the use of shorter wavelength, less than approximately 1 micrometer, for the OCT to achieve higher spatial resolution. An additional advantage of the angled beam path 30 to the irido-corneal angle 13 through the cornea 3 and the anterior chamber 7 is the avoidance of direct laser beam or OCT beam light illuminating the retina 11. As a result, higher average power laser light and OCT light can be used for imaging and surgery, resulting in faster procedures and less tissue movement during the procedure.

Another important feature provided by the integrated surgical system is access to the targeted ocular tissue in the irido-corneal angle 13 in a way that reduces beam discontinuity. To this end, the window and exit lens components of the first optical subsystem are configured to reduce the discontinuity of the optical refractive index between the cornea 3 and the neighboring material and facilitate entering light through the cornea at a steep angle.

Having thus generally described the integrated surgical system and some of its features and advantages, a more detailed description of the system and its component parts follows.

Integrated Surgical System

Figure 7:
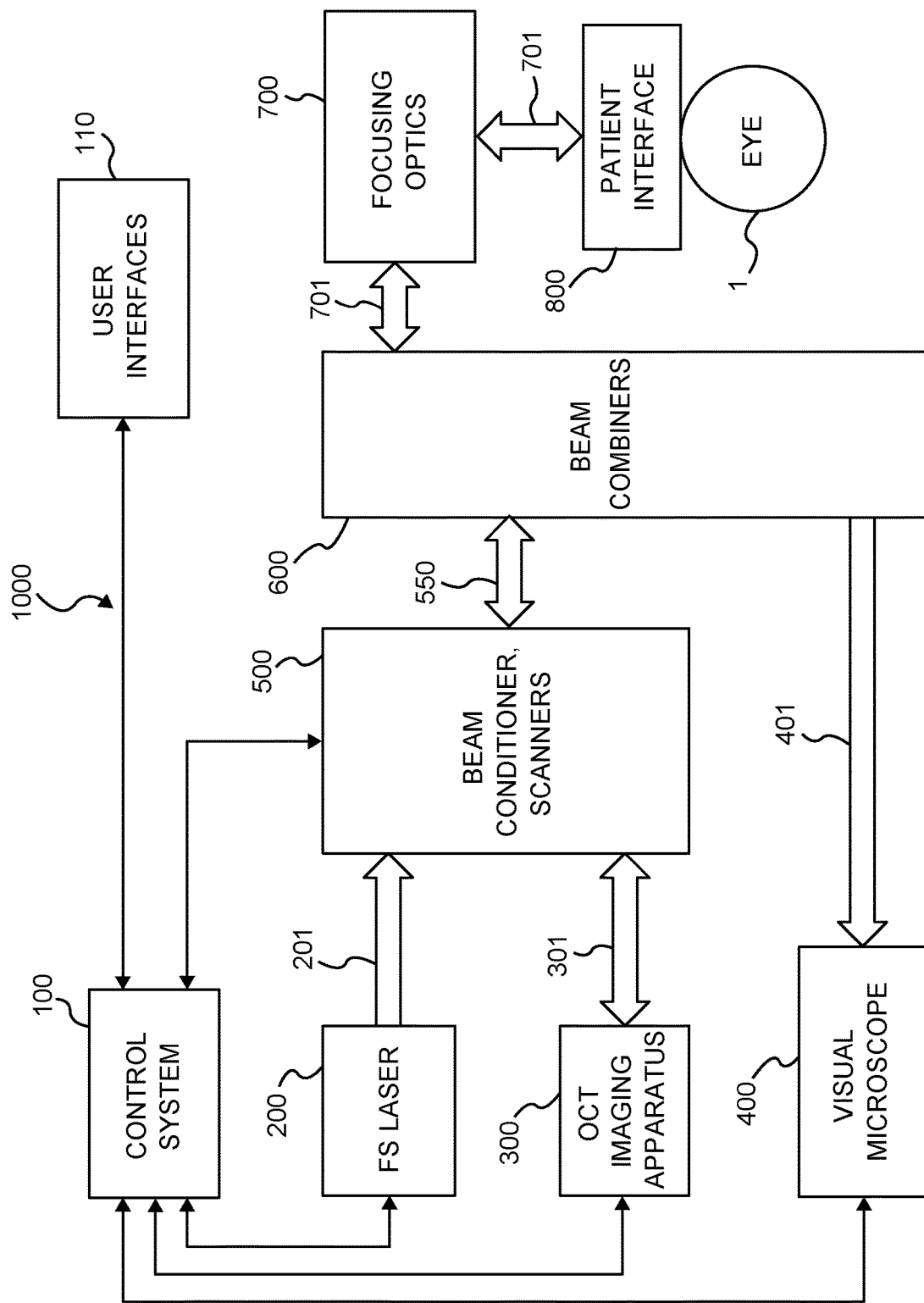
FIG. 7 is a block diagram of an integrated surgical system for non-invasive glaucoma surgery including a control system, a femtosecond laser source, an OCT imaging apparatus, a microscope, beam conditioners and scanners, beam combiners, a focusing objective, and a patient interface.

With reference to FIG. 7, an integrated surgical system 1000 for non-invasive glaucoma surgery includes a control system 100, a surgical component 200, a first imaging component 300 and an optional second imaging component 400. In the embodiment of FIG. 7, the surgical component 200 is a femtosecond laser source, the first imaging component 300 is an OCT imaging apparatus, and the optional second imaging component 400 is a visual observation apparatus, e.g., a microscope, for direct viewing or viewing with a camera. Other components of the integrated surgical system 1000 include beam conditioners and scanners 500, beam combiners 600, a focusing objective 700, and a patient interface 800.

The control system 100 may be a single computer or and plurality of interconnected computers configured to control the hardware and software components of the other components of the integrated surgical system 1000. A user interface 110 of the control system 100 accepts instructions from a user and displays information for observation by the user. Input information and commands from the user include but are not limited to system commands, motion controls for docking the patient's eye to the system, selection of preprogrammed or live generated surgical plans, navigating through menu choices, setting of surgical parameters, responses to system messages, determining and acceptance of surgical plans and commands to execute the surgical plan. Outputs from the system towards the user includes but are not limited to display of system parameters and messages, display of images of the eye, graphical, numerical and textual display of the surgical plan and the progress of the surgery.

The control system 100 is connected to the other components 200, 300, 400, 500 of the integrated surgical system 1000. Control signals from the control system 100 to the femtosecond laser source 200 function to control internal and external operation parameters of the laser source, including for example, power, repetition rate and beam shutter. Control signals from the control system 100 to the OCT imaging apparatus 300 function to control OCT beam scanning parameters, and the acquiring, analyzing and displaying of OCT images.

Laser beams 201 from the femtosecond laser source 200 and OCT beams 301 from the OCT imaging apparatus 300 are directed towards a unit of beam conditioners and scanners 500. Different kind of scanners can be used for the purpose of scanning the laser beam 201 and the OCT beam 301. For scanning transversal to a beam 201, 301, angular scanning galvanometer scanners are available for example from Cambridge Technology, Bedford, Mass., Scanlab, Munich, Germany. To optimize scanning speed, the scanner mirrors are typically sized to the smallest size, which still support the required scanning angles and numerical apertures of the beams at the target locations. The ideal beam size at the scanners is typically different from the beam size of the laser beam 201 or the OCT beam 301, and different from what is needed at the entrance of a focusing objective 700. Therefore, beam conditioners are applied before, after or in between individual scanners. The beam conditioner and scanners 500 includes scanners for scanning the beam transversally and axially. Axial scanning changes the depth of the focus at the target region. Axial scanning can be performed by moving a lens axially in the beam path with a servo or stepper motor.

The laser beam 201 and the OCT beam 301 are combined with dichroic, polarization or other kind of beam combiners 600 to reach a common target volume or surgical volume in the eye. In an integrated surgical system 1000 having a femtosecond laser source 200, an OCT imaging apparatus 300, and a visual observation device 400, the individual beams 201, 301, 401 for each of these components may be individually optimized and may be collinear or non-collinear to one another. The beam combiner 600 uses dichroic or polarization beam splitters to split and recombine light with different wavelength and/or polarization. The beam combiner 600 may also include optics to change certain parameters of the individual beams 201, 301, 401 such as beam size, beam angle and divergence. Integrated visual illumination, observation or imaging devices assist the surgeon in docking the eye to the system and identifying surgical locations.

To resolve ocular tissue structures of the eye in sufficient detail, the imaging components 300, 400 of the integrated surgical system 1000 may provide an OCT beam and a visual observation beam having a spatial resolution of several micrometers. The resolution of the OCT beam is the spatial dimension of the smallest feature that can be recognized in the OCT image. It is determined mostly by the wavelength and the spectral bandwidth of the OCT source, the quality of the optics delivering the OCT beam to the target location in the eye, the numerical aperture of the OCT beam and the spatial resolution of the OCT imaging apparatus at the target location. In one embodiment, the OCT beam of the integrated surgical system has a resolution of no more than 5 µm.

Likewise, the surgical laser beam provided by the femtosecond laser source 200 may be delivered to targeted locations with several micrometer accuracy. The resolution of the laser beam is the spatial dimension of the smallest feature at the target location that can be modified by the laser beam without significantly affecting surrounding ocular tissue. It is determined mostly by the wavelength of the laser beam, the quality of the optics delivering the laser beam to target location in the eye, the numerical aperture of the laser beam, the energy of the laser pulses in the laser beam and the spatial resolution of the laser scanning system at the target location. In addition, to minimize the threshold energy of the laser for photo-disruptive interaction, the size of the laser spot should be no more than approximately 5 µm.

It should be noted that, while the visual observation beam 401 is acquired by the visual observation device 400 using fixed, non-scanning optics, the OCT beam 301 of the OCT imaging apparatus 300 is scanned laterally in two transversal directions. The laser beam 201 of the femtosecond laser source 200 is scanned in two lateral dimensions and the depth of the focus is scanned axially.

For practical embodiments, beam conditioning, scanning and combining the optical paths are certain functions performed on the laser, OCT and visual observation optical beams. Implementation of those functions may happen in a different order than what is indicated in FIG. 7. Specific optical hardware that manipulates the beams to implement those functions can have multiple arrangements with regards to how the optical hardware is arranged. They can be arranged in a way that they manipulate individual optical beams separately, in another embodiment one component may combine functions and manipulates different beams. For example, a single set of scanners can scan both the laser beam 201 and the OCT beam 301. In this case, separate beam conditioners set the beam parameters for the laser beam 201 and the OCT beam 301, then a beam combiner combines the two beams for a single set of scanners to scan the beams. While many combinations of optical hardware arrangements are possible for the integrated surgical system, the following section describes in detail an example arrangement.

Beam Delivery

In the following description, the term beam may—depending on the context—refer to one of a laser beam, an OCT beam, or a visual observation beam. A combined beam refers to two or more of a laser beam, an OCT beam, or a visual observation beam that are either collinearly combined or non-collinearly combined. Example combined beams include a combined OCT/laser beam, which is a collinear or non-colinear combination of an OCT beam and a laser beam, and a combined OCT/laser/visual beam, which is a collinear or non-collinear combination of an OCT beam, a laser beam, and a visual beam. In a collinearly combined beam, the different beams may be combined by dichroic or polarization beam splitters, and delivered along a same optical path through a multiplexed delivery of the different beams. In a non-collinear combined beam, the different beams are delivered at the same time along different optical paths that are separated spatially or by an angle between them. In the description to follow, any of the foregoing beams or combined beams may be generically referred to as a light beam. The terms distal and proximal may be used to designate the direction of travel of a beam, or the physical location of components relative to each other within the integrated surgical system. The distal direction refers to a direction toward the eye; thus an OCT beam output by the OCT imaging apparatus moves in the distal direction toward the eye. The proximal direction refers to a direction away from the eye; thus an OCT return beam from the eye moves in the proximal direction toward the OCT imaging apparatus.

Figure 8:
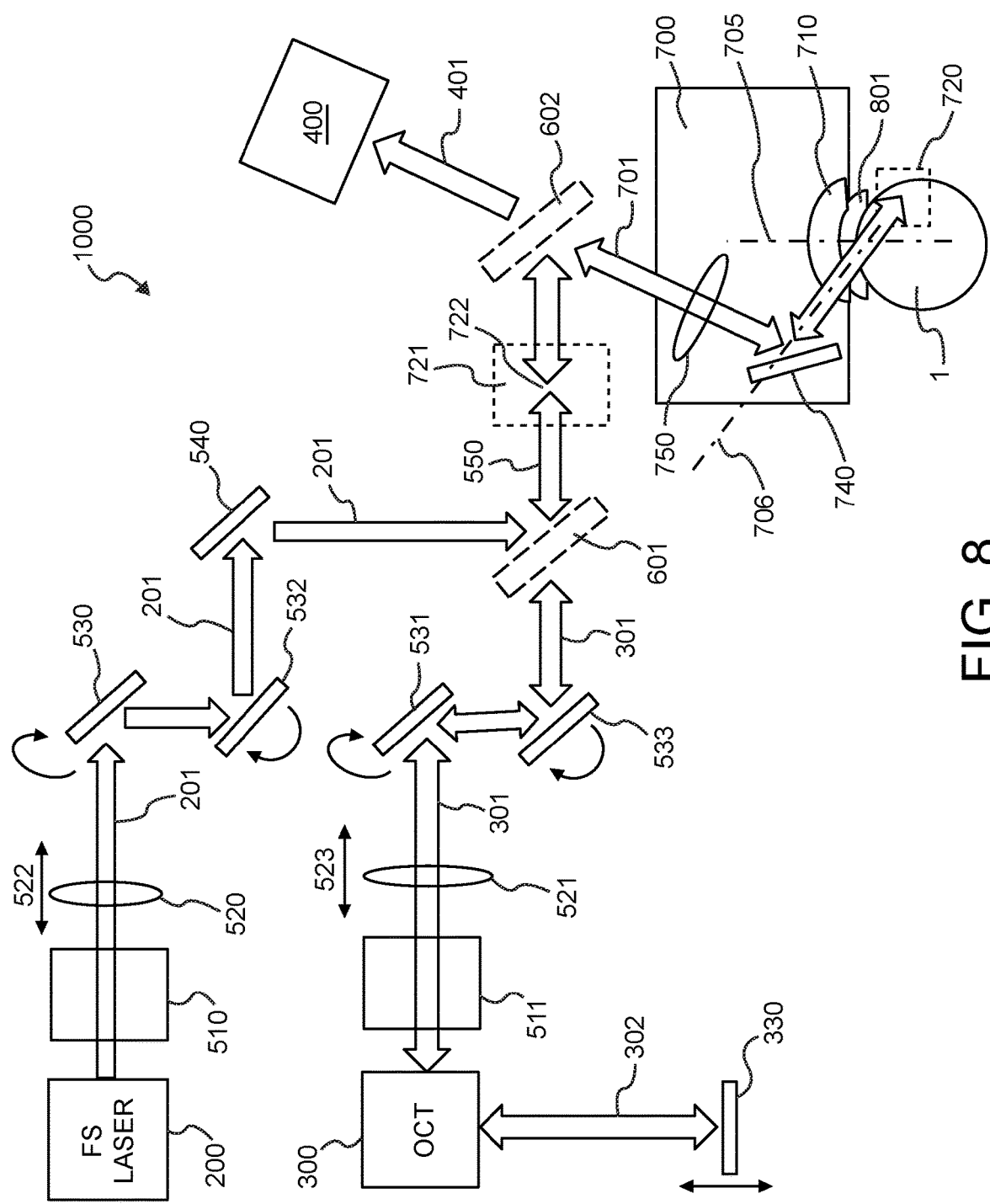
FIG. 8 is a detailed block diagram of the integrated surgical system of FIG. 7.

Referring to FIG. 8, an example integrated surgical system is configured to deliver each of a laser beam 201 and an OCT beam 301 in the distal direction toward an eye 1, and receive each of an OCT return beam and the visual observation beam 401 back from the eye 1. Regarding the delivery of a laser beam, a laser beam 201 output by the femtosecond laser source 200 passes through a beam conditioner 510 where the basic beam parameters, beam size, divergence are set. The beam conditioner 510 may also include additional functions, setting the beam power or pulse energy and shutter the beam to turn it on or off. After existing the beam conditioner 510, the laser beam 210 enters an axial scanning lens 520. The axial scanning lens 520, which may include a single lens or a group of lenses, is movable in the axial direction 522 by a servo motor, stepper motor or other control mechanism. Movement of the axial scanning lens 520 in the axial direction 522 changes the axial distance of the focus of the laser beam 210 at a focal point.

In accordance with a particular embodiment of the integrated surgical system, an intermediate focal point 722 is set to fall within, and is scannable in, the conjugate surgical volume 721, which is an image conjugate of the surgical volume 720, determined by the focusing objective 700. The surgical volume 720 is the spatial extent of the region of interest within the eye where imaging and surgery is performed. For glaucoma surgery, the surgical volume 720 is the vicinity of the irido-corneal angle 13 of the eye.

A pair of transverse scanning mirrors 530, 532 rotated by a galvanometer scanner scan the laser beam 201 in two essentially orthogonal transversal directions, e.g., in the x and y directions. Then the laser beam 201 is directed towards a dichroic or polarization beam splitter 540 where it is reflected toward a beam combining mirror 601 configured to combine the laser beam 201 with an OCT beam 301.

Regarding delivery of an OCT beam, an OCT beam 301 output by the OCT imaging apparatus 300 passes through a beam conditioner 511, an axially moveable focusing lens 521 and a transversal scanner with scanning mirrors 531 and 533. The focusing lens 521 is used set the focal position of the OCT beam in the conjugate surgical volume 721 and the real surgical volume 720. The focusing lens 521 is not scanned for obtaining an OCT axial scan. Axial spatial information of the OCT image is obtained by Fourier transforming the spectrum of the interferometrically recombined OCT return beam 301 and reference beams 302. However, the focusing lens 521 can be used to re-adjust the focus when the surgical volume 720 is divided into several axial segments. This way the optimal imaging spatial resolution of the OCT image can be extended beyond the Rayleigh range of the OCT signal beam, at the expense of time spent on scanning at multiple ranges.

Proceeding in the distal direction toward the eye 1, after the scanning mirrors 531 and 533, the OCT beam 301 is combined with the laser beam 201 by the beam combiner mirror 601. The OCT beam 301 and laser beam 201 components of the combined laser/OCT beam 550 are multiplexed and travel in the same direction to be focused at an intermediate focal point 722 within the conjugate surgical volume 721. After having been focused in the conjugate surgical volume 721, the combined laser/OCT beam 550 propagates to a second beam combining mirror 602 where it is combined with a visual observation beam 401 to form a combined laser/OCT/visual beam 701.

The combined laser/OCT/visual beam 701 traveling in the distal direction then passes through the focusing objective 700, and a window 801 of a patient interface, where the intermediate focal point 722 of the laser beam within the conjugate surgical volume 721 is re-imaged into a focal point in the surgical volume 720. The focusing objective 700 re-images the intermediate focal point 722, through the window 801 of a patient interface, into the ocular tissue within the surgical volume 720.

A scattered OCT return beam 301 from the ocular tissue travels in the proximal direction to return to the OCT imaging apparatus 300 along the same paths just described, in reverse order. The reference beam 302 of the OCT imaging apparatus 300, passes through a reference delay optical path and return to the OCT imaging apparatus from a moveable mirror 330. The reference beam 302 is combined interferometrically with the OCT return beam 301 on its return within the OCT imaging apparatus 300. The amount of delay in the reference delay optical path is adjustable by moving the moveable mirror 330 to equalize the optical paths of the OCT return beam 301 and the reference beam 302. For best axial OCT resolution, the OCT return beam 301 and the reference beam 302 are also dispersion compensated to equalize the group velocity dispersion within the two arms of the OCT interferometer.

When the combined laser/OCT/visual beam 701 is delivered through the cornea 3 and the anterior chamber 7, the combined beam passes through posterior and anterior surface of the cornea at a steep angle, far from normal incidence. These surfaces in the path of the combined laser/OCT/visual beam 701 create excessive astigmatism and coma aberrations that need to be compensated for.

Figure 9A:
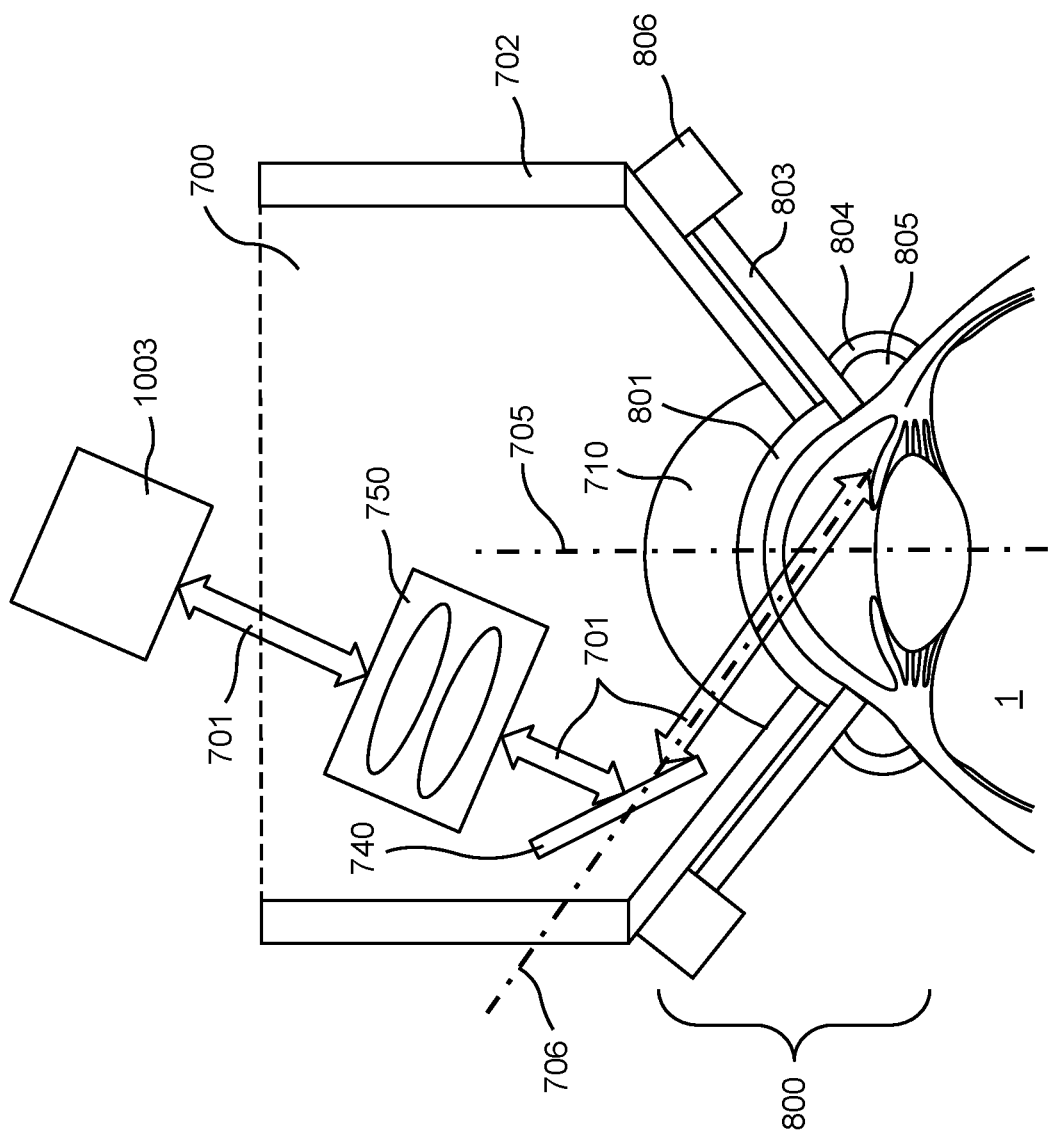
FIGS. 9a and 9b are schematic illustrations of the focusing objective of the integrated surgical system of FIG. 7 coupled to (FIG. 9a) and decoupled from (FIG. 9b) the patient interface of the integrated surgical system of FIG. 7.
Figure 9B:
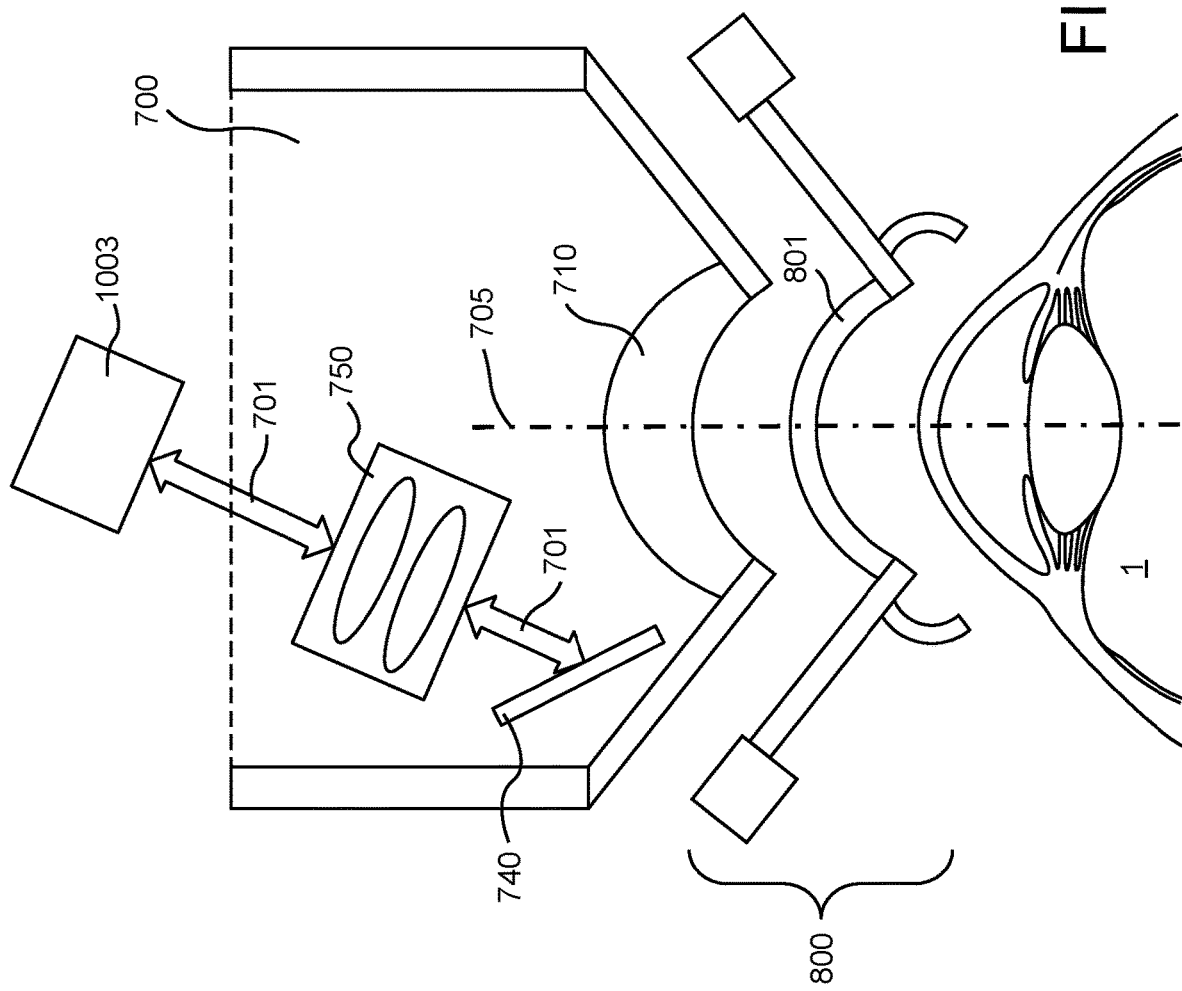

With reference to FIGS. 9a and 9b, in an embodiment of the integrated surgical system 1000, optical components of the focusing objective 700 and patient interface 800 are configured to minimize spatial and chromatic aberrations and spatial and chromatic distortions. FIG. 9a shows a configuration when both the eye 1, the patient interface 800 and the focusing objective 700 all coupled together. FIG. 9b shows a configuration when both the eye 1, the patient interface 800 and the focusing objective 700 all detached from one another.

The patient interface 800 optically and physically couples the eye 1 to the focusing objective 700, which in turn optically couples with other optic components of the integrated surgical system 1000. The patient interface 800 serves multiple functions. It immobilizes the eye relative to components of the integrated surgical system; creates a sterile barrier between the components and the patient; and provides optical access between the eye and the instrument. The patient interface 800 is a sterile, single use disposable device and it is coupled detachably to the eye 1 and to the focusing objective 700 of the integrated surgical system 1000.

Figure 9C:
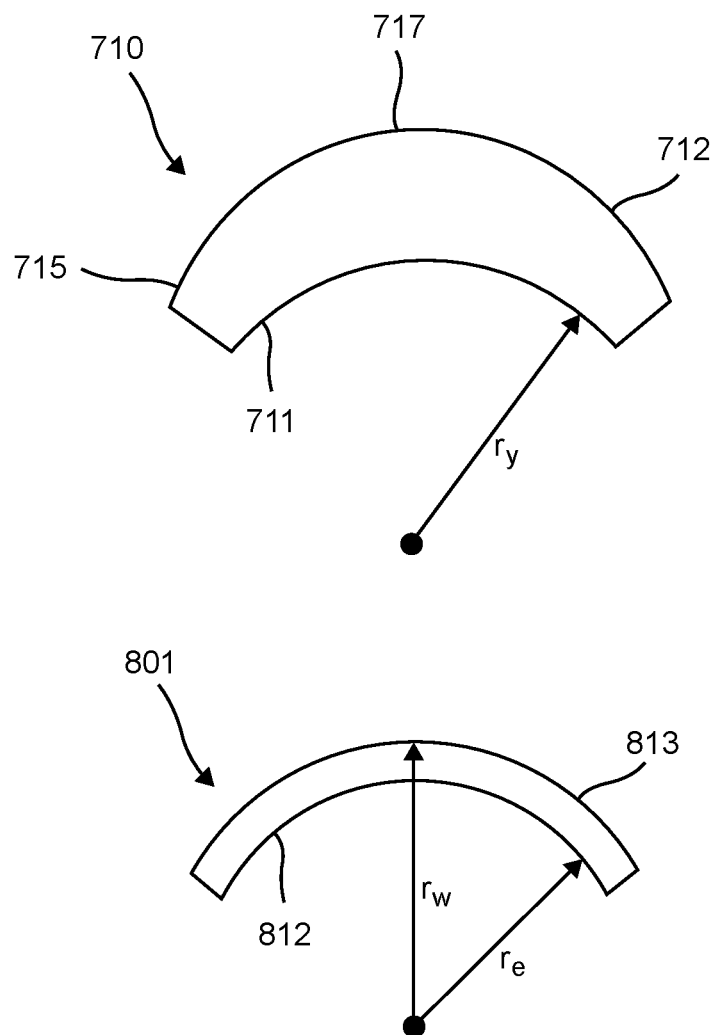
FIG. 9c is a schematic illustration of components of the focusing objective and the patient interface included in FIGS. 9a and 9b.

The patient interface 800 includes a window 801 having an eye-facing, concave surface 812 and an objective-facing, convex surface 813 opposite the concave surface. The window 801 thus has a meniscus form. With reference to FIG. 9c, the concave surface 812 is characterized by a radius of curvature $r_e$, while the convex surface 813 is characterized by a radius of curvature $r_w$. The concave surface 812 is configured to couple to the eye, either through a direct contact or through index matching material, liquid or gel, placed in between the concave surface 812 and the eye 1. The window 801 may be formed of glass and has a refractive index $n_w$. In one embodiment, the window 801 is formed of fused silica and has a refractive index $n_w$ of 1.45. Fused silica has the lowest index from common inexpensive glasses. Fluoropolymers such as the Teflon AF are another class of low index materials that have refractive indices lower than fused silica, but their optical quality is inferior to glasses and they are relatively expensive for high volume production. In another embodiment the window 801 is formed of the common glass BK7 and has a refractive index $n_w$ of 1.50. A radiation resistant version of this glass, BK7G18 from Schott AG, Mainz, Germany, allows gamma sterilization of the patient interface 800 without the gamma radiation altering the optical properties of the window 801.

Returning to FIGS. 9a and 9b, the window 801 is surrounded by a wall 803 of the patient interface 800 and an immobilization device, such as a suction ring 804. When the suction ring 804 is in contact with the eye 1, an annular cavity 805 is formed between the suction ring and the eye. When vacuum applied to the suction ring 804 and the cavity via a vacuum tube a vacuum pump (not shown in FIGS. 9a and 9b), vacuum forces between the eye and the suction ring attach the eye to the patient interface 800 during surgery. Removing the vacuum releases or detach the eye 1.

The end of the patient interface 800 opposite the eye 1 includes an attachment interface 806 configured to attach to the housing 702 of the focusing objective 700 to thereby affix the position of the eye relative to the other components of the integrated surgical system 1000. The attachment interface 806 can work with mechanical, vacuum, magnetic or other principles and it is also detachable from the integrated surgical system.

The focusing objective 700 includes an aspheric exit lens 710 having an eye-facing, concave surface 711 and a convex surface 712 opposite the concave surface. The exit lens 710 thus has a meniscus form. While the exit lens 710 shown in FIGS. 9a and 9b is an aspheric lens giving more design freedom, in other configurations the exit lens may be a spherical lens. Alternatively, constructing the exit lens 710 as a compound lens, as opposed to a singlet, allows more design freedom to optimize the optics while preserving the main characteristics of the optical system as presented here. With reference to FIG. 9c, the concave surface 711 is characterized by a radius of curvature $r_y$, while the convex surface 712 is characterized by an aspheric shape. The aspheric convex surface 712 in combination with the spherical concave surface 711 result in an exit lens 710 having varying thickness, with the outer perimeter edges 715 of the lens being thinner than the central, apex region 717 of the lens. The concave surface 711 is configured to couple to the convex surface 813 of the window 801. In one embodiment, the exit lens 710 is formed of fused silica and has a refractive index $n_x$ of 1.45.

Figure 10A:
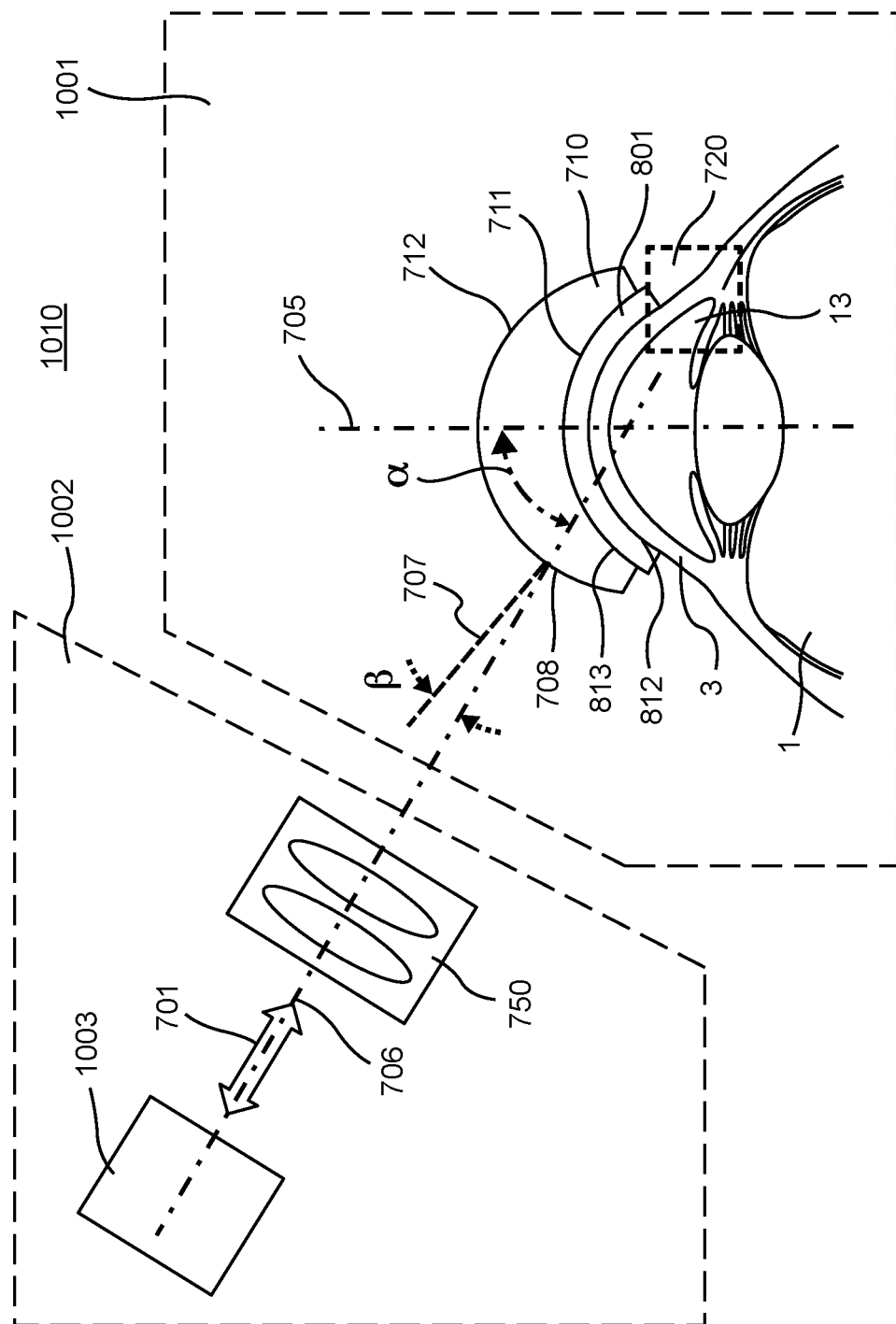
FIGS. 10a and 10b are schematic illustrations of components of the integrated surgical system of FIGS. 7 and 8 functionally arranged to form a first optical system and a second optical subsystem that enable access to the to the irido-corneal angle along the angled beam path of FIG. 6.
Figure 10B:
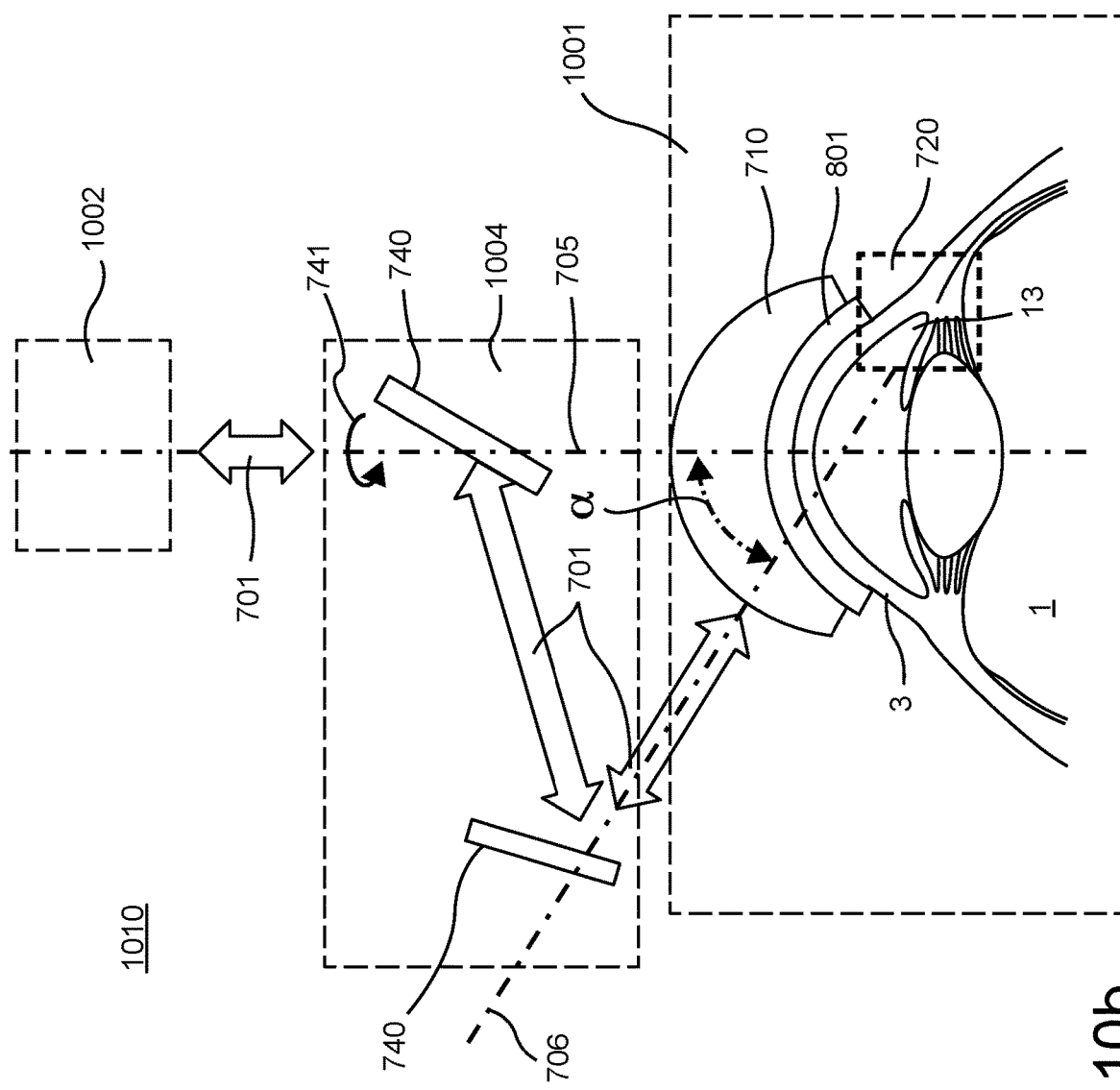
Figure 10C:
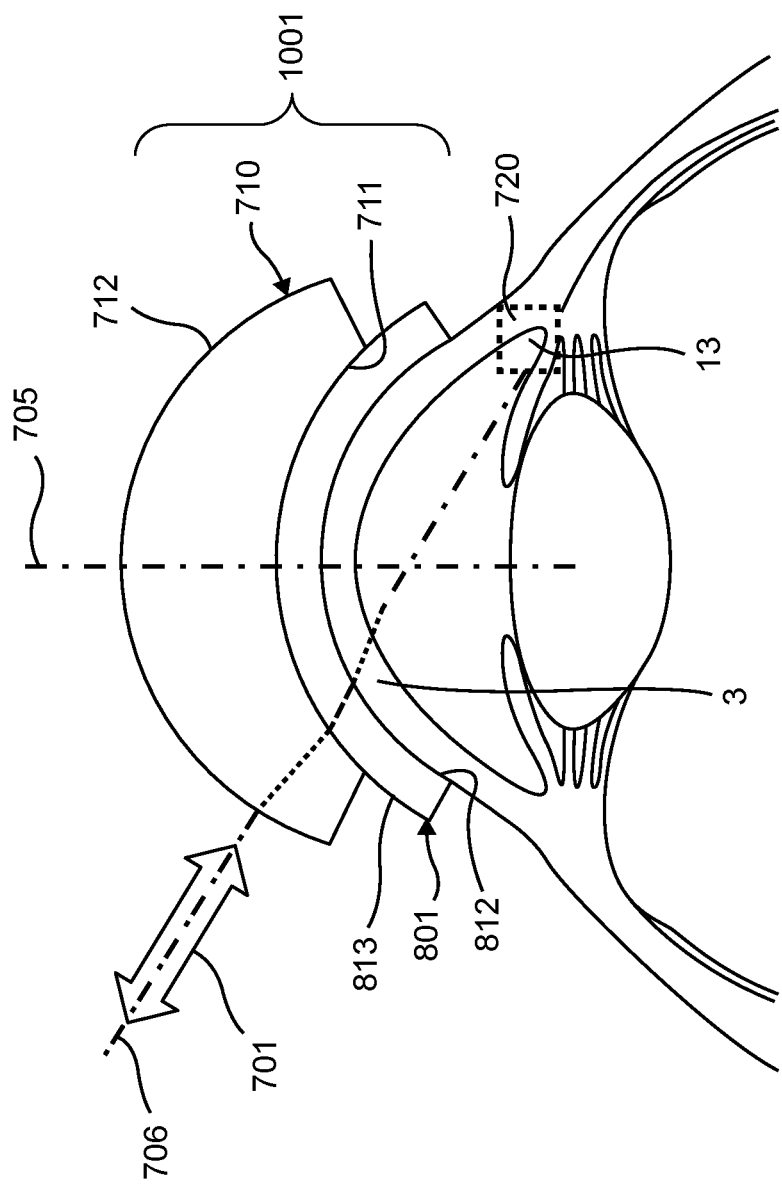
FIG. 10c is a schematic illustration of a beam passing through the first optical subsystem of FIGS. 10a and 10b and into the eye.

FIGS. 10a and 10b are schematic illustrations of components of the integrated surgical system of FIGS. 7 and 8 functionally arranged to form an optical system 1010 having a first optical subsystem 1001 and a second optical subsystem 1002 that enable access to a surgical volume 720 in the irido-corneal angle. Each of FIGS. 10a and 10b include components of the focusing objective 700 and the patient interface 800 of FIG. 9a. However, for simplicity, the entirety of the focusing objective and the patient interface are not included in FIGS. 10a and 10b. Also, for additional simplicity in FIG. 10a, the planar beam-folding mirror 740 of FIGS. 9a and 9b is not included and the combined laser/OCT/visual beam 701 shown in FIG. 9a is unfolded or straightened out. It is understood by those skilled in the art that adding or removing planar beam folding mirrors does not alter the principal working of the optical system formed by the first optical subsystem and the second optical subsystem. FIG. 10c is a schematic illustration of a beam passing through the first optical subsystem of FIGS. 10a and 10b.

With reference to FIG. 10a, a first optical subsystem 1001 of the integrated surgical system 1000 includes the exit lens 710 of a focusing objective 700 and the window 801 of a patient interface 800. The exit lens 710 and the window 801 are arranged relative to each other to define a first optical axis 705. The first optical subsystem 1001 is configured to receive a beam, e.g., a combined laser/OCT/visual beam 701, incident at the convex surface 712 of the exit lens 710 along a second optical axis 706, and to direct the beam toward a surgical volume 720 in the irido-corneal angle 13 of the eye.

During a surgical procedure, the first optical subsystem 1001 may be assembled by interfacing the convex surface 813 of the window 801 with the concave surface 711 of the exit lens 710. To this end, a focusing objective 700 is docked together with a patient interface 800. As a result, the concave surface 711 of the exit lens 710 is coupled to the convex surface 813 of the window 801. The coupling may be by direct contact or through a layer of index matching fluid. For example, when docking the patient interface 800 to focusing objective 700, a drop of index matching fluid can be applied between the contacting surfaces to eliminate any air gap that may be between the two surfaces 711, 813 to thereby help pass the combined laser/OCT/visual beam 701 through the gap with minimal Fresnel reflection and distortion.

In order to direct the beam toward the surgical volume 720 in the irido-corneal angle 13 of the eye, the first optical subsystem 1001 is designed to account for refraction of the beam 701 as it passes through the exit lens 710, the window 801 and the cornea 3. To this end, and with reference to FIG. 10c, the refractive index $n_x$ of the exit lens 710 and the refractive index $n_w$ of the window 801 are selected in view of the refractive index $n_c$ of the cornea 3 to cause appropriate beam bending through the first optical subsystem 1001 so that when the beam 701 exits the subsystem and passes through the cornea 3, the beam path is generally aligned to fall within the irido-corneal angle 13.

Continuing with reference to FIG. 10c and beginning with the interface between the window 801 and the cornea 3. Too steep of an angle of incidence at the interface where the combined laser/OCT/visual beam 701 exits the window 801 and enters the cornea 3, i.e., at the interface between the concave surface 812 of the window and the convex surface of the cornea 3, can create excessive refraction and distortion. To minimize refraction and distortion at this interface, in one embodiment of the first optical subsystem 1001, the refractive index of the window 801 is closely matched to the index of the cornea 3. For example, as describe above with reference to FIGS. 9a and 9b, the window 801 may have a refractive index lower than 1.42 to closely match the cornea 3, which has a refractive index of 1.36.

Excessive refraction and distortion at the interface where the combined laser/OCT/visual beam 701 exits the window 801 and enters the cornea 3 may be further compensated for by controlling the bending of the beam 701 as it passed through the exit lens 710 and the window 801. To this end, in one embodiment of the first optical subsystem 1001 the index of refraction $n_w$ of the window 801 is larger than each of the index of refraction $n_x$ of the exit lens 710 and the index of refraction $n_c$ of the cornea 3. As a result, at the interface where the combined laser/OCT/visual beam 701 exits the exit lens 710 and enters the window 801, i.e., interface between the concave surface 711 of the exit lens and the convex surface 813 of the window, the beam passes through a refractive index change from high to low that cause the beam to bend in a first direction. Then, at the interface where the combined laser/OCT/visual beam 701 exits the window 801 and enters the cornea 3, i.e., interface between the concave surface 812 of the exit lens and the convex surface of the cornea, the beam passes through a refractive index change from low to high that cause the beam to bend in a second direction opposite the first direction.

The shape of the window 801 is chosen to be a meniscus lens. As such, the incidence angle of light has similar values on both surfaces 812, 813 of the window 801. The overall effect is that at the convex surface 813 the light bends away from the surface normal and at the concave surface 812 the light bends towards the surface normal. The effect is like when light passes through a plan parallel plate. Refraction on one surface of the plate is compensated by refraction on the other surface a light passing through the plate does not change its direction. Refraction at the entering, convex surface 712 of the exit lens 710 distal to the eye is minimized by setting the curvature of the entering surface such that angle of incidence β of light 701 at the entering surface is close to a surface normal 707 to the entering surface at the intersection point 708.

Here, the exit lens 710, the window 801, and the eye 1 are arranged as an axially symmetric system with a first optical axis 705. In practice, axial symmetry is an approximation because of manufacturing and alignment inaccuracies of the optical components, the natural deviation from symmetry of the eye and the inaccuracy of the alignment of the eye relative to the window 801 and the exit lens 710 in a clinical setting. But, for design and practical purposes the eye 1, the window 801, and the exit lens 710 are considered as an axially symmetric first optical subsystem 1001.

With continued reference to FIG. 10a, a second optical subsystem 1002 is optically coupled to the first optical subsystem 1001 at an angle α relative to the first optical axis 705 of the first optical subsystem 1001. The advantage of this arrangement is that the both optical subsystems 1001, 1002 can be designed at a much lower numerical aperture compared to a system where all optical components are designed on axis with a common optical axis.

The second optical subsystem 1002 includes a relay lens 750 that, as previously described with reference to FIG. 8, generates a conjugate surgical volume 721 of the surgical volume 720 within the eye. The second optical subsystem 1002 includes various other components collectively indicated as an optical subsystem step 1003. Referring to FIG. 8, these components may include a femtosecond laser source 200, an OCT imaging apparatus 300, a visual observation device 400, beam conditioners and scanners 500, and beam combiners 600.

The second optical subsystem 1002 may include mechanical parts (not shown) configured to rotate the entire subsystem around the first optical axis 705 of the first optical subsystem 1001. This allows optical access to the whole 360-degree circumference of the irido-corneal angle 13 of the eye 1.

With reference to FIG. 10b, flexibility in arranging the first and second optical subsystems 1001, 1002, relative to each other may be provided by an optical assembly 1004 interposed between the optical output of the second optical subsystem 1002 and the optical input of the first optical subsystem 1001. In one embodiment, the optical assembly 1004 may include one or more planar beam-folding mirrors 740, prisms (not shown) or optical gratings (not shown) configured to receive the optical output, e.g., combined laser/OCT/visual beam 701, of the second optical subsystem 1002, change or adjust the direction of the combined laser/OCT/visual beam, and direct the beam to the optical input of the first optical subsystem 1001 while preserving the angle α between the first optical axis 705 and the second optical axis 706.

In another configuration, the optical assembly 1004 of planar beam-folding mirrors 740 further includes mechanical parts (not shown) configured to rotate 741 the assembly around the first optical axis 705 of the first optical subsystem 1001 while keeping the second optical subsystem 1002 stationary. Accordingly, the second optical axis 706 of the second optical subsystem 1002 can be rotated around the first optical axis 705 of the first optical subsystem 1001. This allows optical access to the whole 360-degree circumference of the irido-corneal angle 13 of the eye 1.

With considerations described above with reference to FIGS. 9a, 9b and 9c, the design of the first optical subsystem 1001 is optimized for angled optical access at an angle α relative to the first optical axis 705 of the first optical subsystem 1001. Optical access at the angle α compensates for optical aberrations of the first optical subsystem 1001. Table 1 shows the result of the optimization at access angle α=72 degrees with Zemax optical design software package. This design is a practical embodiment for image guided femtosecond glaucoma surgery.

TABLE 1

| Surface | Structure and Material | Refractive index | Radius [mm] | Center Thickness [mm] |
|---|---|---|---|---|
| concave surface 711, convex surface 712 | Exit lens 710 of focusing objective. Fused silica | 1.45 | −10 | 4.5 |
| concave surface 812, convex surface 813 | Window 801 of patient interface. BK7G18 | 1.50 | −10.9 | 1.0 |
| 3 | Cornea | 1.36 | −7.83 | 0.54 |
| 8 | Aqueous humor | 1.32 | −6.53 | 3.5 |
| Target | Ophthalmic tissue | 1.38 | N/A | 0 to 1 mm |

This design produces diffraction limited focusing of 1030 nm wavelength laser beams and 850 nm wavelength OCT beams with numerical aperture (NA) up to 0.2. In one design, the optical aberrations of the first optical subsystem are compensated to a degree that the Strehl ratio of the first optical subsystem for a beam with numerical aperture larger than 0.15 at the irido-corneal angle is larger than 0.9. In another design, the optical aberrations of the first optical subsystem are partially compensated, the remaining uncompensated aberrations of the first optical system are compensated by the second optical subsystem to a degree that the Strehl ratio of the combined first and second optical subsystem for a beam with numerical aperture larger than 0.15 at the irido-corneal angle is larger than 0.9.

Calibration

The femtosecond laser source 200, OCT imaging apparatus 300, and visual observation device 400 of the integrated surgical system 1000 are first individually calibrated to ensure their internal integrity and then cross-calibrated for system integrity. The essential part of system calibration is to ensure that the when the surgical focus of a laser beam 201 is commanded to a location of a surgical volume 720, as identified by the OCT imaging apparatus and/or the visual observation device 400, the achieved location of the focus matches the commanded location of the focus within a certain tolerance, typically within 5 to 10 µm. Also, graphical and cursor outputs, images, overlays displayed on a user interface 110, such as a computer monitor, and user inputs of ocular tissue surgical volume 720 locations accepted from the user interface 110 should correspond to actual locations in tissue within predetermined tolerances of similar accuracy.

One embodiment of this spatial calibration procedure starts with imaging calibrated scales and scaling magnifications of the OCT imaging apparatus 300 and/or the visual observation device 400 and their displays in a way that the scale value on the display matches the real scale of the calibration target. Then laser calibration patters are exposed or burned into transparent calibration targets, and the calibration patterns are subsequently imaged. Then, the intended patterns and the actual burned patterns are compared with the imaging system of the integrated surgical system 1000 or by a separate microscope. If they do not match within the specified tolerance, the scaling parameters of the surgical patterns are re-scaled by adjusting the scaling of the laser beam scanners. This procedure is iterated, if necessary, until all spatial calibrations are within tolerance.

Minimally Invasive Surgical Treatments

Figure 11:
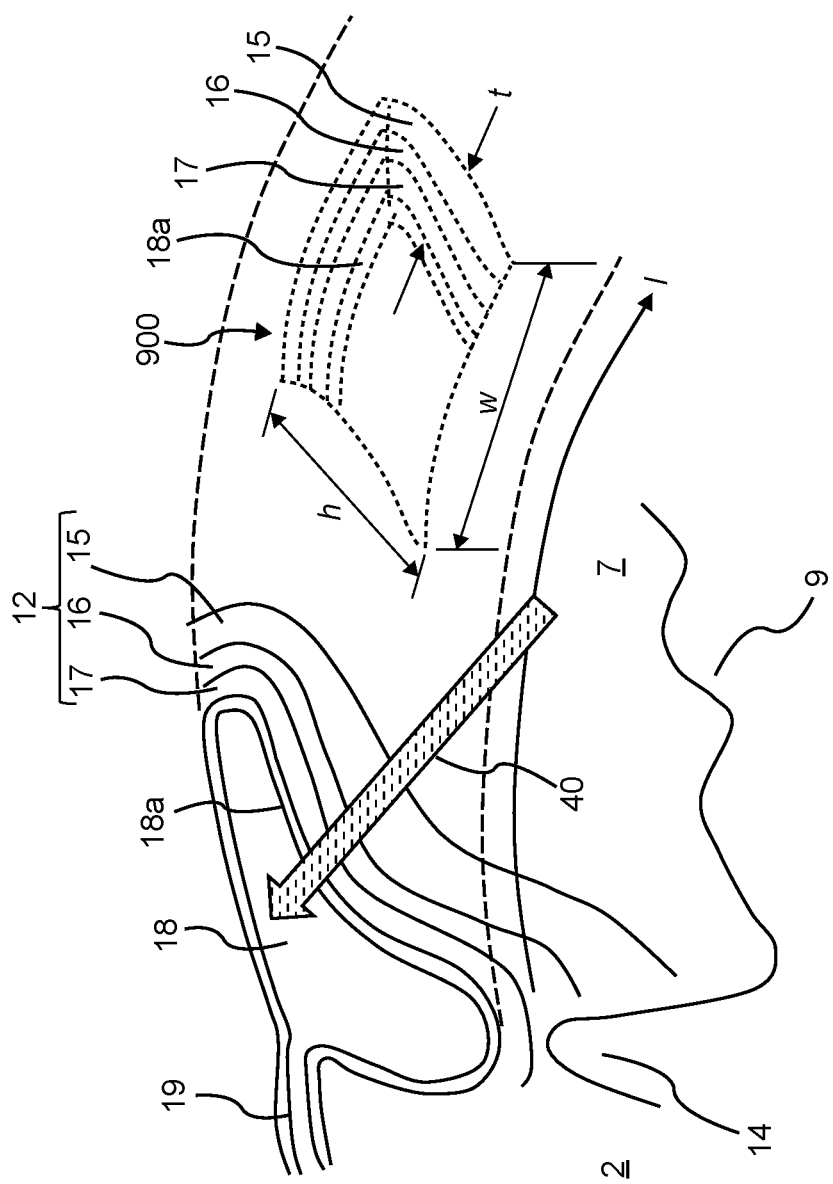
FIG. 11 is a three-dimensional schematic illustration of anatomical structures in the irido-corneal angle, including the trabecular meshwork, Schlemm's canal, a collector channel branching from the Schlemm's canal, and a surgical volume of ocular tissue to be treated by the integrated surgical system of FIG. 7.

FIG. 11 is a three-dimensional schematic illustration of anatomical structures of the eye relevant to the surgical treatment enabled by the integrated surgical system 1000. To reduce the IOP, laser treatment targets ocular tissues that affect the trabecular outflow pathway 40. These ocular tissues may include the trabecular meshwork 12, the scleral spur 14, the Schlemm's canal 18, and the collector channels 19. The trabecular meshwork 12 has three layers, the uveal 15, the corneoscleral meshwork 16, and the juxtacanalicular tissue 17. These layers are porous and permeable to aqueous, with the uveal 15 being the most porous and permeable, followed by the corneoscleral meshwork 16. The least porous and least permeable layer of the trabecular meshwork 12 is the juxtacanalicular tissue 17. The inner wall 18a of the Schlemm's canal 18, which is also porous and permeable to aqueous, has characteristics similar to the juxtacanalicular tissue 17.

Figure 12:
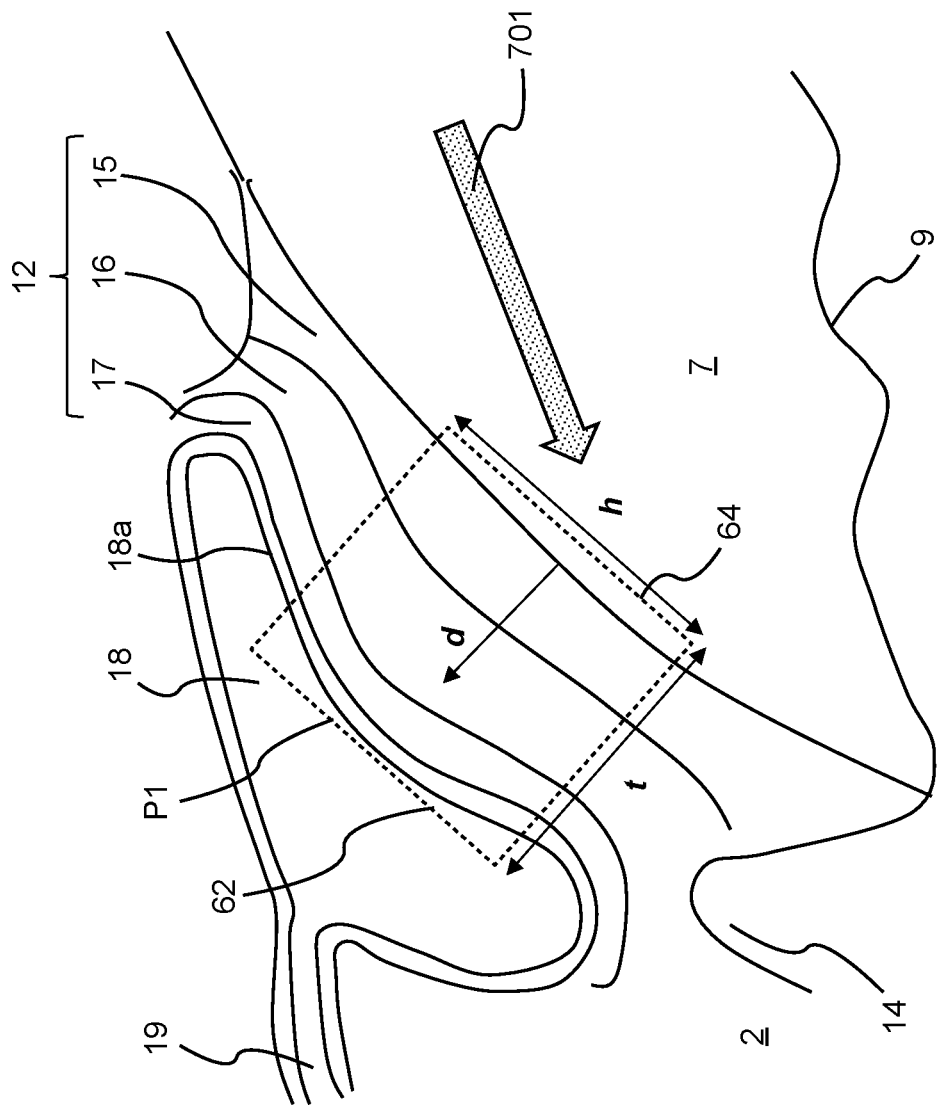
FIG. 12 is a two-dimensional schematic illustration of anatomical structures in the irido-corneal angle and a laser treatment pattern to be applied by the integrated surgical system of FIG. 7 to affect a surgical volume of ocular tissue between the Schlemm's canal and the anterior chamber as shown in FIG. 11.
Figure 12:
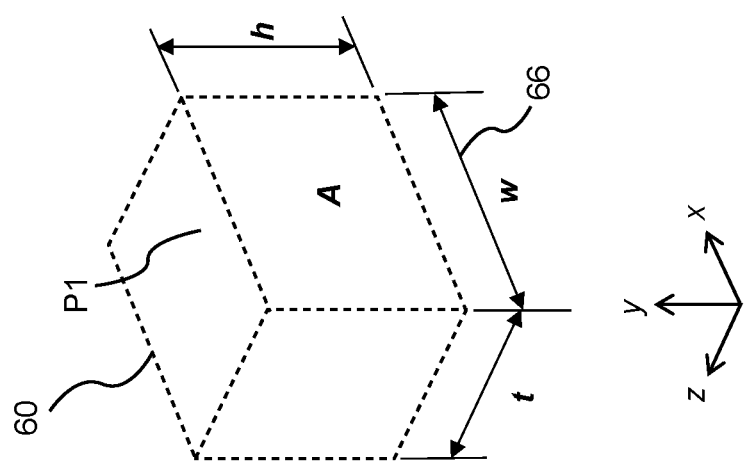
Figure 13:
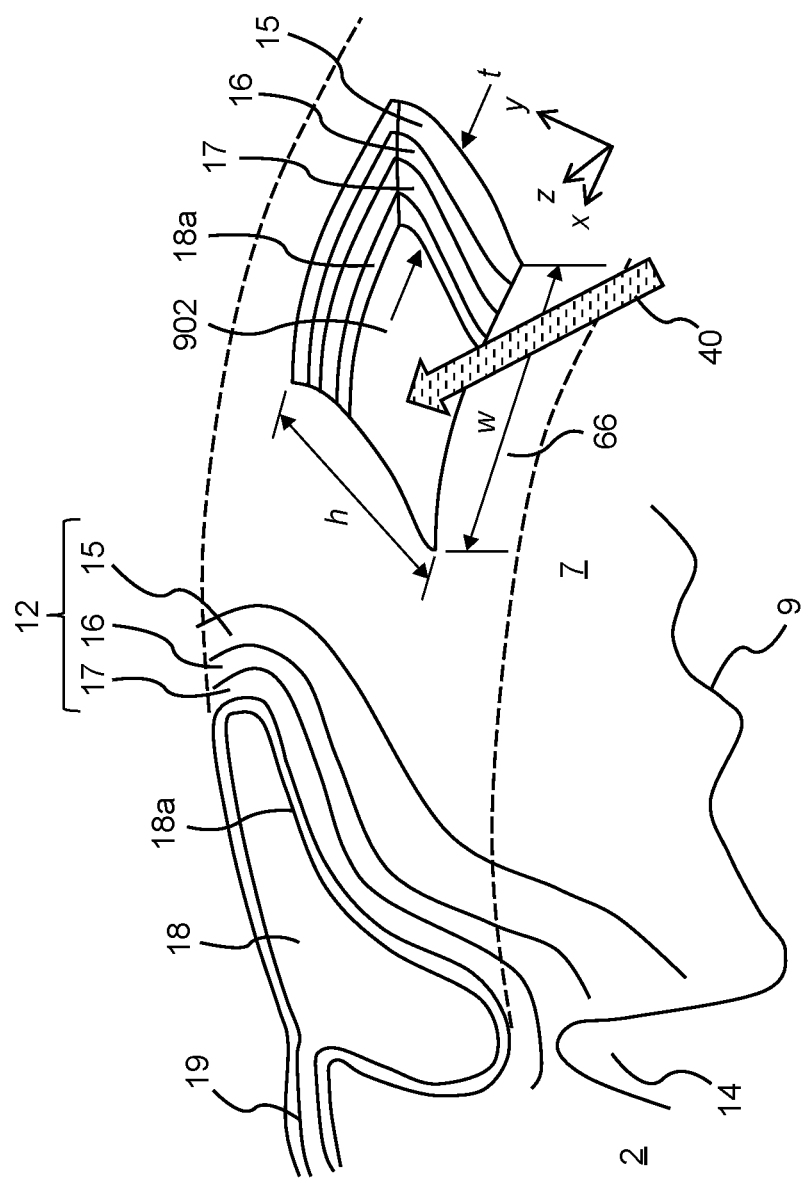
FIG. 13 is a three-dimensional schematic illustration of FIG. 11 subsequent to treatment of the surgical volume of ocular tissue by a laser based on the laser treatment pattern of FIG. 12 that forms an opening between the Schlemm's canal and the anterior chamber.

FIG. 12 includes a three-dimensional illustration of a treatment pattern P1 to be applied by the integrated surgical system 1000 to affect the surgical volume 900 of ocular tissue shown in FIG. 11, and a two-dimensional schematic illustration of the treatment pattern P1 overlaying anatomical structures to be treated. FIG. 13 is a three-dimensional schematic illustration of the anatomical structures of the eye including an opening 902 through the that results from the application of the laser treatment pattern of FIG. 12. The opening 902 provides and outflow pathway 40 that reduces the flow resistance in the ocular tissue to increase aqueous flow from the anterior chamber 7 into the Schlemm's canal 18 and thereby reduce the IOP of the eye.

Surgical treatments reduce outflow pathway resistance while minimizing ocular tissue modification through design and selection of laser treatment patterns. A treatment pattern is considered to define a collection of a laser-tissue interaction volumes, referred to herein as cells. The size of a cell is determined by the extent of the influence of the laser-tissue interaction. When the laser spots, or cells, are spaced close along a line, the laser creates a narrow, microscopic channel. A wider channel can be created by closely spacing a multitude of laser spots within the cross section of the channel. The arrangement of the cells may resemble the arrangement of atoms in a crystal structure.

With reference to FIG. 12, a treatment pattern P1 may be in the form of a cubic structure that encompasses individual cells arranged in regularly spaced rows, columns and sheets or layers. The treatment pattern P1 may be characterized by x, y, z dimensions, with x, y, z coordinates of the cells being calculated sequentially from neighbor to neighbor in the order of a column location (x coordinate), a row location (y coordinate), and a layer location (z coordinate). A treatment pattern P1 as such, defines a three-dimensional model of ocular tissue to be modified by a laser or a three-dimensional model of ocular fluid to be affected by a laser.

A treatment pattern P1 is typically defined by a set of surgical parameters. The surgical parameters may include one or more of a treatment area A that represents a surface area or layer of ocular tissue through which the laser will travel. The treatment area A is determined by the treatment height, h, and the lateral extent of the treatment, w. A treatment thickness t that represents the level to which the laser will cut into the ocular tissue from the distal extent or border of the treatment volume at or near Schlemm's canal 18 to the proximal extent or border at or near the surface of the trabecular meshwork 12. Thus, a laser applied in accordance with a treatment pattern may affect or produce a surgical volume that resembles the three-dimensional model of the treatment pattern, or may affect fluid located in an interior of an eye structure resembled by the three-dimensional model.

Additional surgical parameters define the placement of the surgical volume or affected volume within the eye. For example, with reference to FIGS. 11 and 12, placement parameters may include one or more of a location l that represents where the treatment is to occur relative to the circumferential angle of the eye, and a treatment depth d that represents a position of the three-dimensional model of ocular tissue or ocular fluid within the eye relative to a reference eye structure. In the following, the treatment depth d is shown and described relative to the region where the anterior chamber 7 meets the trabecular meshwork 12. Together, the treatment pattern and the placement parameters define a treatment plan.

A femtosecond laser provides highly localized, non-thermal photo-disruptive laser-tissue interaction with minimal collateral damage to surrounding ocular tissue. Photo-disruptive interaction of the laser is utilized in optically transparent tissue. The principal mechanism of laser energy deposition into the ocular tissue is not by absorption but by a highly nonlinear multiphoton process. This process is effective only at the focus of the pulsed laser where the peak intensity is high. Regions where the beam is traversed but not at the focus are not affected by the laser. Therefore, the interaction region with the ocular tissue is highly localized both transversally and axially along the laser beam.

With reference to FIGS. 11 and 12, in accordance with embodiments disclosed herein a surgical volume 900 of ocular tissue to be treated is identified by the integrated surgical system 1000 and a treatment pattern P1 corresponding to the surgical volume is designed by the integrated surgical system. Alternatively, the treatment pattern P1 may be designed first, and then an appropriate surgical volume 900 for applying the treatment pattern may be identified. The surgical volume 900 of ocular tissue may comprise portions of the trabecular meshwork 12 and the Schlemm's canal 18. For example, the surgical volume 900 of ocular tissue shown in FIG. 11 includes portions of the uveal 15, the corneoscleral meshwork 16, the juxtacanalicular tissue 17, and the inner wall 18a of the Schlemm's canal 18. The treatment pattern P1 defines a laser scanning procedure whereby a laser is focused at different depth locations in ocular tissue and then scanned in multiple directions to affect a three-dimensional volume of tissue comprising multiple sheets or layers of affected tissue.

With reference to FIGS. 12 and 13, during a laser scanning procedure, a surgical laser 701 may scan ocular tissue in accordance with the treatment pattern P1 to form an opening 902 that extends from the anterior chamber 7, through each of the uveal 15, the corneoscleral meshwork 16, the juxtacanalicular tissue 17 of the trabecular meshwork 12, and the inner wall 18a of the Schlemm's canal 18. While the example opening 902 in FIG. 13 is depicted as a continuous, single lumen defining a fluid pathway, the opening may be defined an arrangement of adjacent pores forming a sponge like structure defining a fluid pathway or a combination thereof. While the example opening 902 in FIG. 13 is in the shape of a cube, the opening may have other geometric shapes.

The movement of the laser as it scans to affect the surgical volume 900 follows the treatment pattern P1, which is defined by a set of surgical parameters that include a treatment area A and a thickness t. The treatment area A is defined by a width w and a height h. The width may be defined in terms of a measure around the circumferential angle. For example, the width w may be defined in terms of an angle, e.g., 90 degrees, around the circumferential angle.

Referring to FIGS. 11 and 12, an initial placement of the laser focus within the eye is defined by a set of placement parameters, including a depth d and a location l. The location l defines a point around the circumferential angle of the eye at which laser treatment will begin, while the depth d defines a point between the anterior chamber 7 and the Schlemm's canal 18 where the laser treatment begins or ends. The depth d is measured relative to the region where the anterior chamber 7 meets the trabecular meshwork 12. Thus, a first point that is closer to the Schlemm's canal 18 side of the trabecular meshwork 12 may be described as being deeper than a second point that is closer to the anterior chamber 7 side of the trabecular meshwork 12. Alternatively, the second point may be described as being shallower than the first point.

With reference to FIG. 13, the opening 902 resulting from laser application of the treatment pattern P1 resembles the surgical volume 900 and is characterized by an area A and thickness t similar to those of the surgical volume and the treatment pattern. The thickness t of the resulting opening 902 extends from the anterior chamber 7 and through the inner wall 18a of the Schlemm's canal 18, while the area A defines the cross-section size of the opening 902.

In accordance with embodiments disclosed herein, during a laser scanning procedure, a laser focus is moved to different depths d in ocular tissue and then scanned in two lateral dimensions or directions as defined by a treatment pattern P1 to affect a three-dimensional volume 900 of ocular tissue comprising multiple sheets or layers of affected tissue. The two lateral dimensions are generally orthogonal to the axis of movement of the laser focus. With reference to FIG. 13, the movement of a laser focus during laser scanning is described herein with reference to x, y, and z directions or axes, wherein: 1) movement of the laser focus to different depths d through the thickness t of treatment pattern P1 or the volume 900 of tissue corresponds to movement of the focus along the z axis, 2) movement of the laser focus in two dimensions or directions orthogonal to the z axis corresponds to movement of the laser focus along the width w of the treatment pattern P1 or the volume 900 of tissue in the x direction, and movement of the laser focus along the height h of the treatment pattern P1 or the volume 900 of tissue in the y direction.

As used herein scanning of the laser focus generally corresponds to a raster type movement of the laser focus in the x direction, the y direction, and the z direction. The laser focus may be located at a point in the z direction and then raster scanned in two dimensions or directions, in the x direction and the y direction. The focal point of the laser in the z direction may be referred to as a depth d within the treatment pattern P1 or the volume 900 of tissue. The two direction raster scanning of the laser focus defines a layer of laser scanning, which in turn produces a layer of laser-affected tissue.

During laser scanning, pulse shots of a laser are delivered to tissue within the volume of ocular tissue corresponding to the treatment pattern P1. Because the laser interaction volume is small, on the order of a few micrometers (m), the interaction of ocular tissue with each laser shot of a repetitive laser breaks down ocular tissue locally at the focus of the laser. Pulse duration of the laser for photo-disruptive interaction in ocular tissue can range from several femtoseconds to several nanoseconds and pulse energies from several nanojoules to tens of microjoules. The laser pulses at the focus, through multiphoton processes, breaks down chemical bonds in the molecules, locally photo-dissociate tissue material and create gas bubbles in wet tissue. The breakdown of tissue material and mechanical stress from bubble formation fragments the tissue and create clean continuous cuts when the laser pulses are laid down in proximity to one another along geometrical lines and surfaces.

Table 2 includes examples of treatment pattern parameters and surgical laser parameters for treating tissue. The range of the parameter set is limited by practical ranges for the repetition rate of the laser and the scanning speed of the scanners.

TABLE 2

| Tissue treated | Treatment pattern dimensions w[mm], h[mm], t[mm] | Opening cross section A [mm$^2$] | Cell size w[μm], h[μm], t[μm] | Laser average power [W] | Laser repetition rate [kHz] | Laser pulse energy [μJ] | Procedure time [s] |
|---|---|---|---|---|---|---|---|
| Trabecular meshwork | 1.5, 0.2, 0.2 | 0.3 | 3, 3, 3 | 0.9 | 300 | 3 | 7.4 |
| Trabecular meshwork | 2, 0.2, 0.2 | 0.4 | 4, 4, 4 | 1 | 200 | 5 | 6.3 |

With reference to FIGS. 11, 12, 13, 14a and 14b, in one type of laser scanning procedure, the scanning begins at the end of the treatment pattern P1 adjacent the anterior chamber 7 and proceeds in a direction that generally corresponds to the direction of propagation of the laser 701. More specifically, and with reference to FIG. 14a, the laser scanning proceeds in the z direction toward an anatomical structure, e.g., the inner wall 18a of the Schlemm's canal 18, while the direction of propagation of the laser 701 also proceeds toward same anatomical structure, e.g., the inner wall 18a of the Schlemm's canal 18.

Laser scanning in this manner, however, may be ineffective at producing the desired opening 902 between the anterior chamber 7 and the Schlemm's canal 18 due to interference by gas bubbles produced during laser application. As noted above, femtosecond lasers generate a very short pulse of optical energy. When a beam of such pulses is focused to a very small volume of space characterized by a small cross-sectional area, a non-linear effect occurs within the focus spot. When such a focus spot is directed onto tissue, the tissue is photodisrupted (broken down) leaving a small bubble of gas. This process is essentially non-thermal and requires a tiny amount of energy. The result is that the surrounding tissue is not affected.

However, when a femtosecond laser beam is scanned over the surface of a tissue, the laser treatment of this initial surface layer generates a layer of bubbles over the area of the treatment. When the laser scans the layer of tissue below or deeper than the initial surface layer, these bubbles create a shadow effect that scatters the incident laser light, effectively blocking further treatment of the tissue. This renders further laser treatment of tissue beneath or deeper that the initial surface layer ineffective.

Figure 14A:
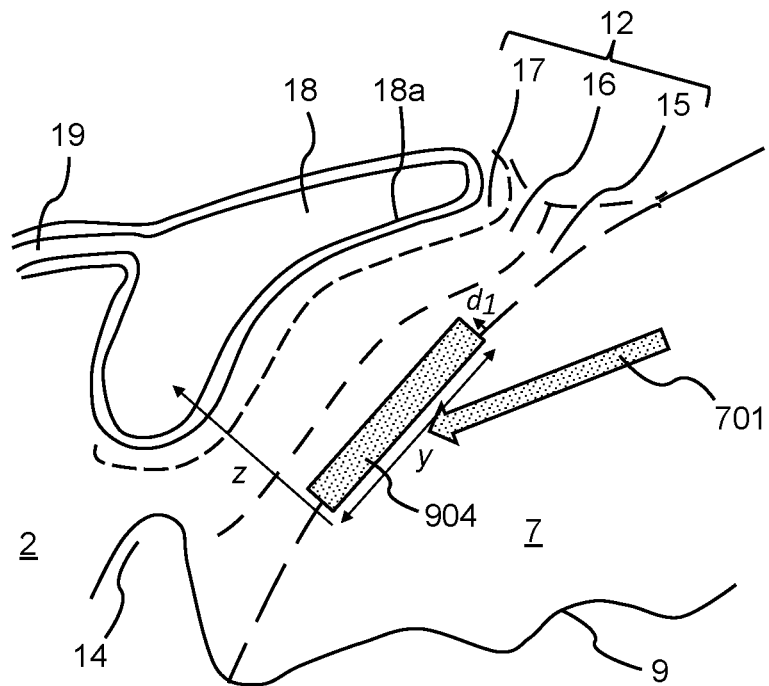
FIGS. 14a and 14b are a series of schematic illustrations of a laser scanning process based on the treatment pattern of FIG. 12, where the scanning begins adjacent the anterior chamber and proceeds toward the Schlemm's canal.
Figure 14B:
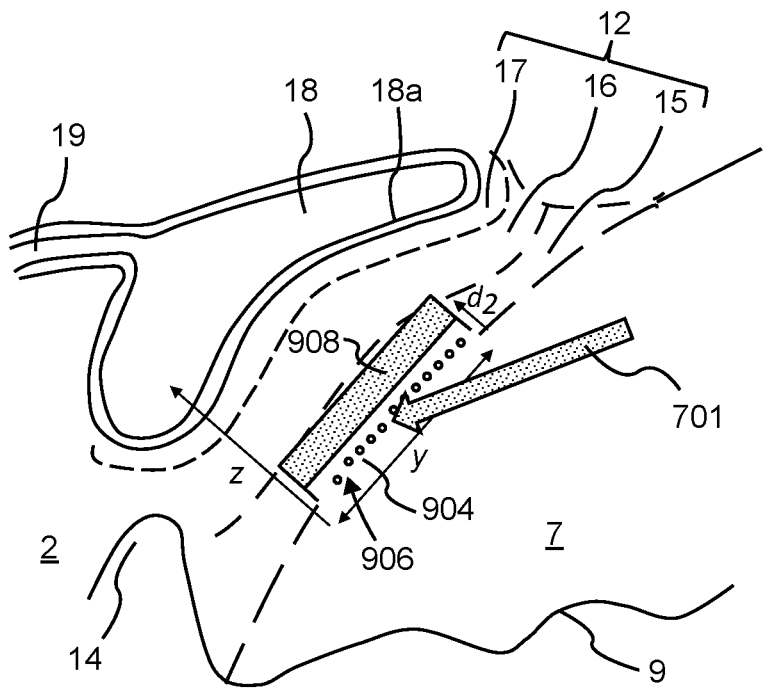

An example of this effect within the context of glaucoma surgery is illustrated in FIGS. 14a and 14b. In FIG. 14a, the focus of the laser beam 701 is initially located at a depth $d_1$. This depth $d_1$ places the laser focus in an initial layer 904 of tissue. For example, initial layer 904 of tissue may be at the interface between the uveal 15 of the trabecular meshwork 12 and the anterior chamber 7. In this instance, this depth location of the laser focus is referred to a null depth and the initial layer 904 to be treated corresponds to the surface of the uveal 15 facing the anterior chamber 7. Once the laser focus is positioned at the initial depth $d_1$, the focus is scanned in multiple directions while being maintained at the initial depth. With reference to FIG. 14a, the multiple directions are the x direction and y direction, where the x direction is into the plane of FIG. 14a.

With reference to FIG. 14b, the raster scanning in the multiple directions results in the photodisruption of the initial layer 904 of tissue and the formation of a layer of bubbles 906 at the initial layer of tissue. The focus of the laser beam 701 is then moved in the z direction toward the inner wall 18a of the Schlemm's canal 18 to another depth $d_2$. This depth $d_2$ places the laser focus at a subsequent layer 908 of tissue deeper than the initial layer 904. For example, the deeper layer of tissue may comprise the uveal 15 of the trabecular meshwork 12. Once the laser focus is positioned at the subsequent layer 908, the focus is raster scanned in multiple directions while being maintained at that depth. However, in this instance, the layer of bubbles 906 scatters the incident laser light, effectively blocking further treatment of the tissue at the subsequent layer 908.

With reference to FIGS. 11, 12, 13, 15a-15g, in accordance with embodiments disclosed the above ineffective laser treatment is avoided by implementing a laser scanning procedure, whereby the laser scanning begins at the end of the treatment pattern P1 adjacent the Schlemm's canal 18 and proceeds in a direction generally opposite to or against the direction of propagation of the laser 701. More specifically, and with reference to FIG. 15a, the laser scanning starts at an anatomical structure, e.g., the inner wall 18a of the Schlemm's canal 18 and proceeds away from that structure in the z direction toward the anterior chamber 7, while the direction of propagation of the laser 701 proceeds toward the that structure.

With this scanning procedure, the laser beam of femtosecond pulses is focused within a volume of ocular tissue at an initial depth or distance from a surface of the volume of tissue. An initial layer of tissue at the initial depth is treated, which generates a layer of bubbles at the area of the initial layer. After treatment of the initial layer of tissue, the laser is refocused to a subsequent layer of tissue that is shallower than the initial layer of tissue, i.e., at a depth that is closer to the surface of the volume of ocular tissue than the initial depth. Since the layer of bubbles at the area of the initial layer is below the second layer, the bubbles do not obstruct the second layer. This process is repeated until the laser scans, layer-by-layer through the volume of ocular tissue to the surface of the volume of tissue.

Figure 15A:
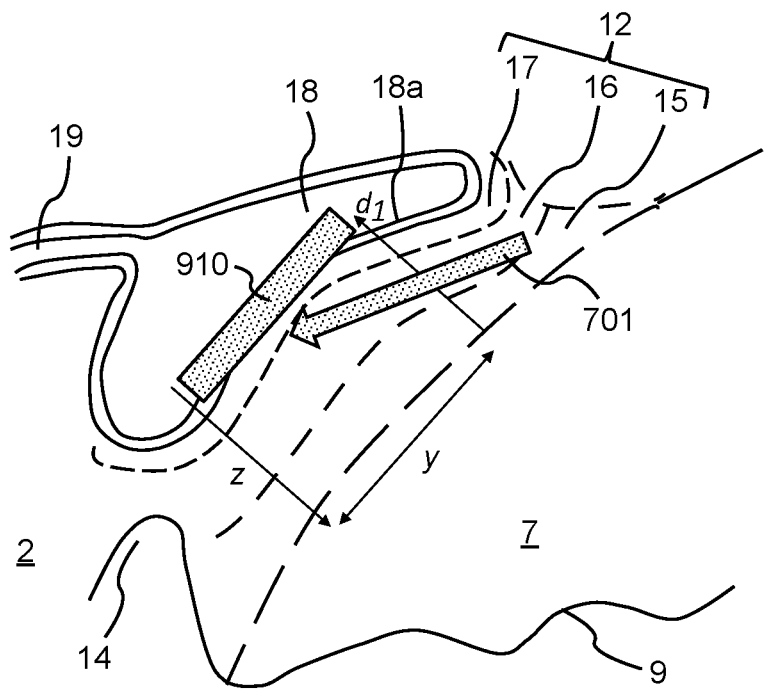
FIGS. 15a-15g are a series of schematic illustrations of a laser scanning process based on the treatment pattern of FIG. 12, where the scanning begins adjacent the Schlemm's canal and proceeds toward the anterior chamber.

An example of this scanning procedure within the context of glaucoma surgery is illustrated in FIGS. 15a-15g. In FIG. 15a, the focus of the laser beam 701 is initially located at a depth $d_1$. This depth $d_1$ places the laser focus in an initial layer 910 of tissue. For example, initial layer 910 of tissue may comprise the inner wall 18a of the Schlemm's canal 18. Once the laser focus is positioned at the initial depth $d_1$, the focus is scanned in multiple directions while being maintained at the initial depth $d_1$. With reference to FIG. 15a, the multiple directions are the x direction and y direction, where the x direction is into the plane of FIG. 15a.

Figure 15B:
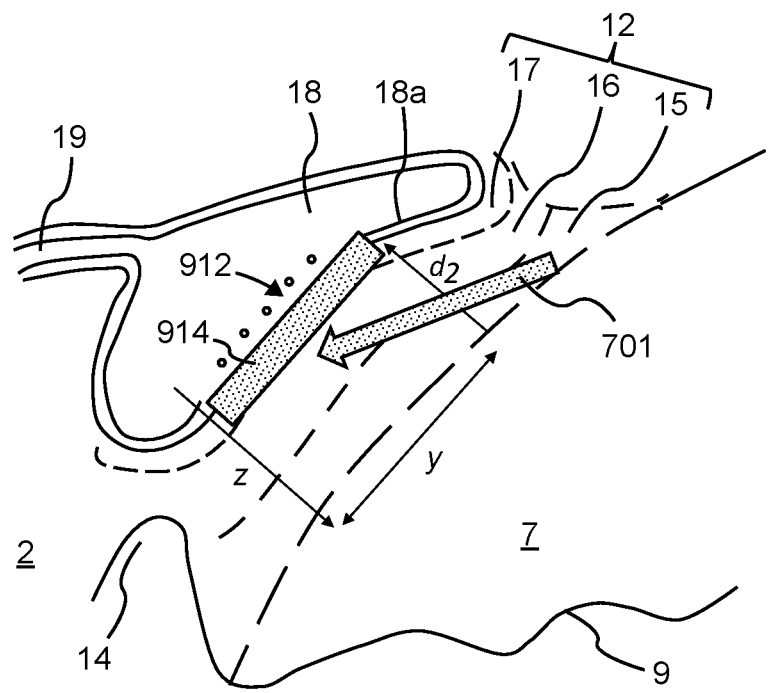

With reference to FIG. 15b, the laser scanning in multiple directions results in the photodisruption of the initial layer 910 of tissue and the formation of a layer of bubbles 912 at the location of the initial layer of tissue. The focus of the laser beam 701 is then moved in the z direction toward the anterior chamber 7 to a subsequent depth $d_2$. The subsequent depth $d_2$ places the laser focus at a subsequent layer 914 of tissue less deep than the initial layer 910 of tissue. For example, the subsequent layer 914 of tissue may comprise a portion of the inner wall 18a of the Schlemm's canal 18, the juxtacanalicular tissue 17, and the corneoscleral meshwork 16. Once the laser focus is positioned at the subsequent depth $d_2$, the focus is scanned in multiple directions while being maintained at the subsequent depth $d_2$. Since the layer of bubbles 912 is beneath the subsequent layer 914, the bubbles do not obstruct laser access to or block photodisruption of the subsequent layer.

Figure 15C:
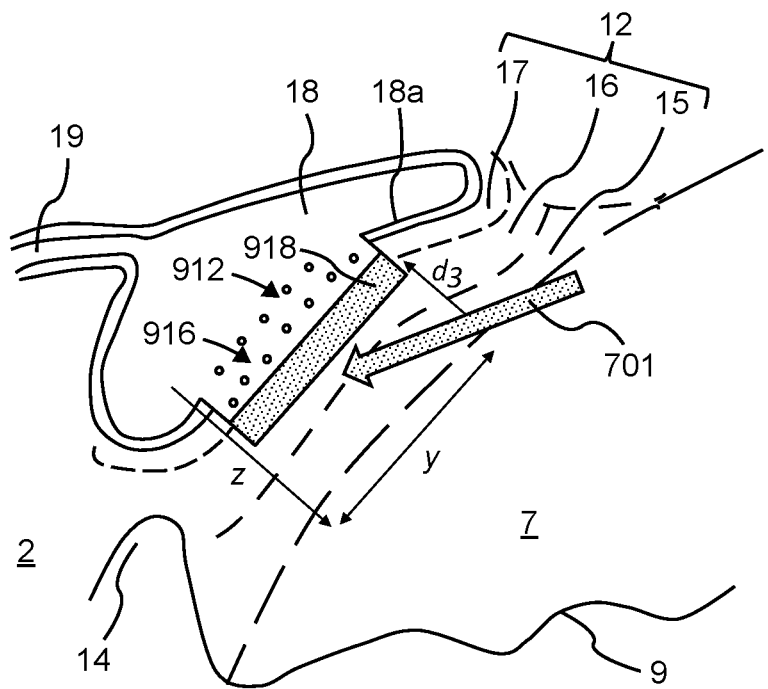

With reference to FIG. 15c, the laser scanning in multiple directions results in the photodisruption of the subsequent layer 914 of tissue and the formation of a layer of bubbles 916 at the location of the subsequent layer of tissue. The focus of the laser beam 701 is then moved in the z direction toward the anterior chamber 7 to a subsequent depth $d_3$. The subsequent depth $d_3$ places the laser focus at a subsequent layer 918 of tissue less deep than the subsequent layer 914 of tissue. For example, the subsequent layer 914 of tissue may comprise a portion of the juxtacanalicular tissue 17 and the corneoscleral meshwork 16. Once the laser focus is positioned at the subsequent depth $d_3$, the focus is scanned in multiple directions while being maintained at the subsequent depth $d_3$. Since the layers of bubbles 912, 916 are beneath the subsequent layer 918, the bubbles do not obstruct laser access to or block photodisruption of the subsequent layer.

Figure 15D:
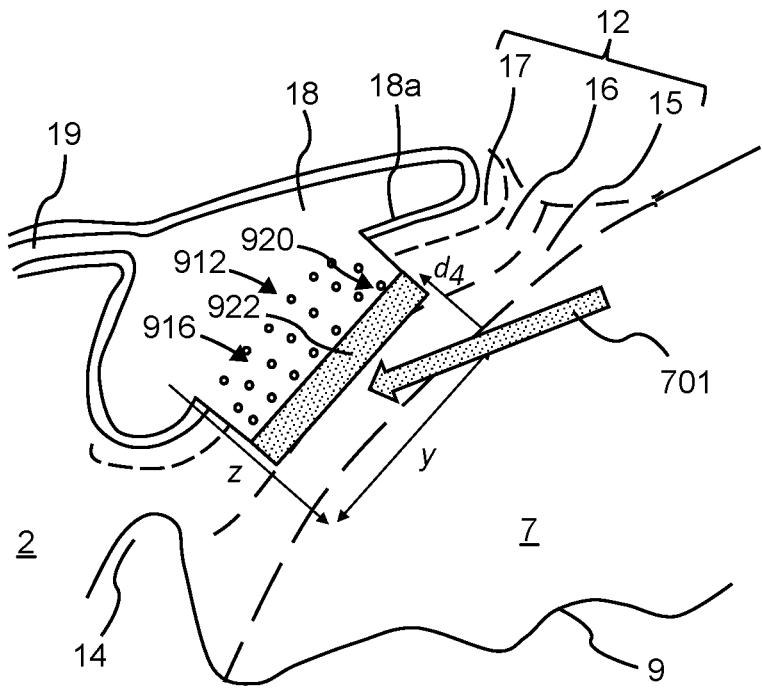

With reference to FIG. 15d, the laser scanning in multiple directions results in the photodisruption of the subsequent layer 918 of tissue and the formation of a layer of bubbles 920 at the location of the subsequent layer of tissue. The focus of the laser beam 701 is then moved in the z direction toward the anterior chamber 7 to a subsequent depth $d_4$. The subsequent depth $d_4$ places the laser focus at a subsequent layer 922 of tissue less deep than the subsequent layer 918 of tissue. For example, the subsequent layer 922 of tissue may comprise a portion of the corneoscleral meshwork 16 and the uveal 15. Once the laser focus is positioned at the subsequent depth $d_4$, the focus is scanned in multiple directions while being maintained at the subsequent depth $d_4$. Since the layers of bubbles 912, 916, 920 are beneath the subsequent layer 922, the bubbles do not obstruct laser access to or block photodisruption of the subsequent layer.

Figure 15E:
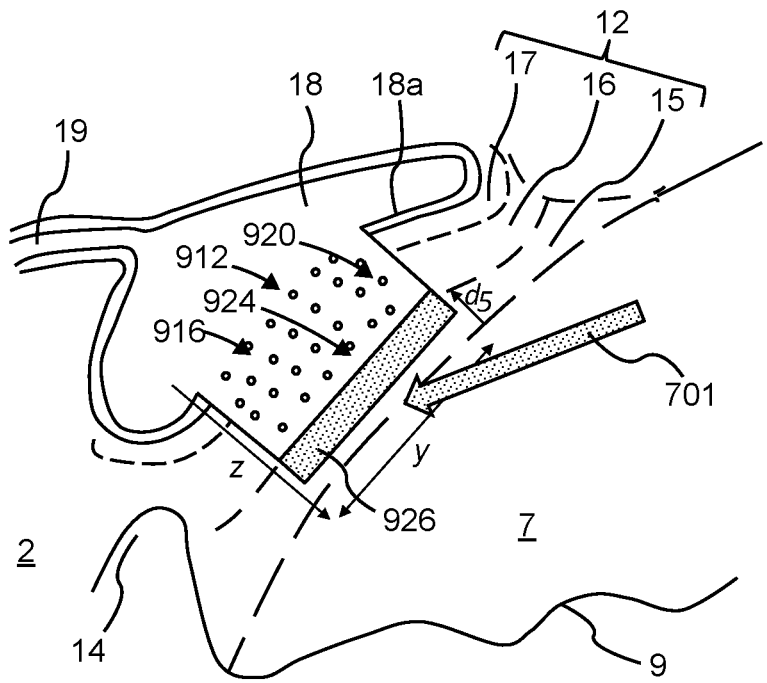

With reference to FIG. 15e, the laser scanning in multiple directions results in the photodisruption of the subsequent layer 922 of tissue and the formation of a layer of bubbles 924 at the location of the subsequent layer of tissue. The focus of the laser beam 701 is then moved in the z direction toward the anterior chamber 7 to a subsequent depth $d_5$. The subsequent depth $d_5$ places the laser focus at a subsequent layer 926 of tissue less deep than the subsequent layer 922 of tissue. For example, the subsequent layer 926 of tissue may comprise the uveal 15. Once the laser focus is positioned at the subsequent depth $d_5$, the focus is scanned in multiple directions while being maintained at the subsequent depth $d_5$. Since the layers of bubbles 912, 916, 920, 924 are beneath the subsequent layer 926, the bubbles do not obstruct laser access to or block photodisruption of the subsequent layer.

Figure 15F:
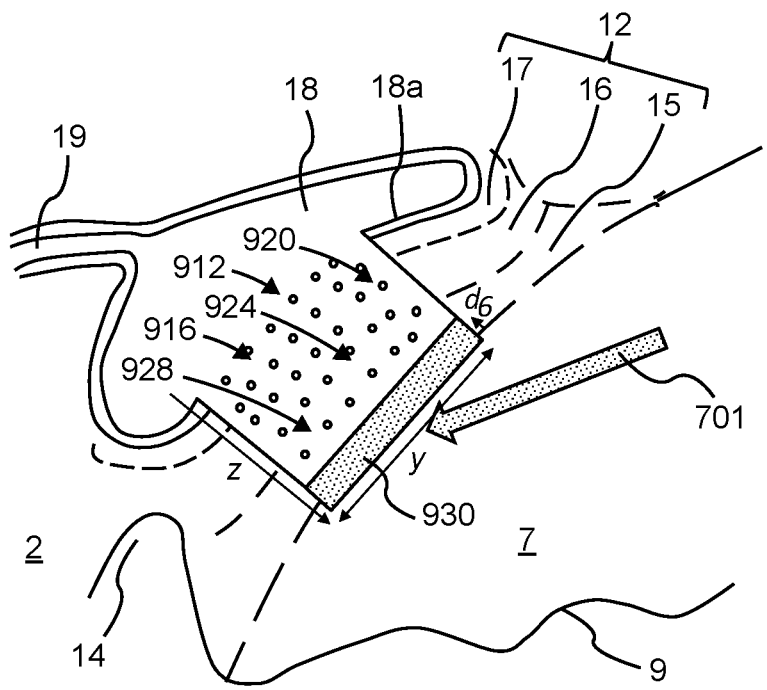

With reference to FIG. 15f, the laser scanning in multiple directions results in the photodisruption of the subsequent layer 926 of tissue and the formation of a layer of bubbles 928 at the location of the subsequent layer of tissue. The focus of the laser beam 701 is then moved in the z direction toward the anterior chamber 7 to a subsequent depth $d_6$. The subsequent depth $d_6$ places the laser focus at a subsequent layer 930 of tissue less deep than the subsequent layer 926 of tissue. For example, the subsequent layer 930 of tissue may comprise the uveal 15 and the inner surface of the uveal facing the anterior chamber 7. Once the laser focus is positioned at the subsequent depth $d_6$, the focus is scanned in multiple directions while being maintained at the subsequent depth $d_6$. Since the layers of bubbles 912, 916, 920, 924, 928 are beneath the subsequent layer 930, the bubbles do not obstruct laser access to or block photodisruption of the subsequent layer.

Figure 15G:
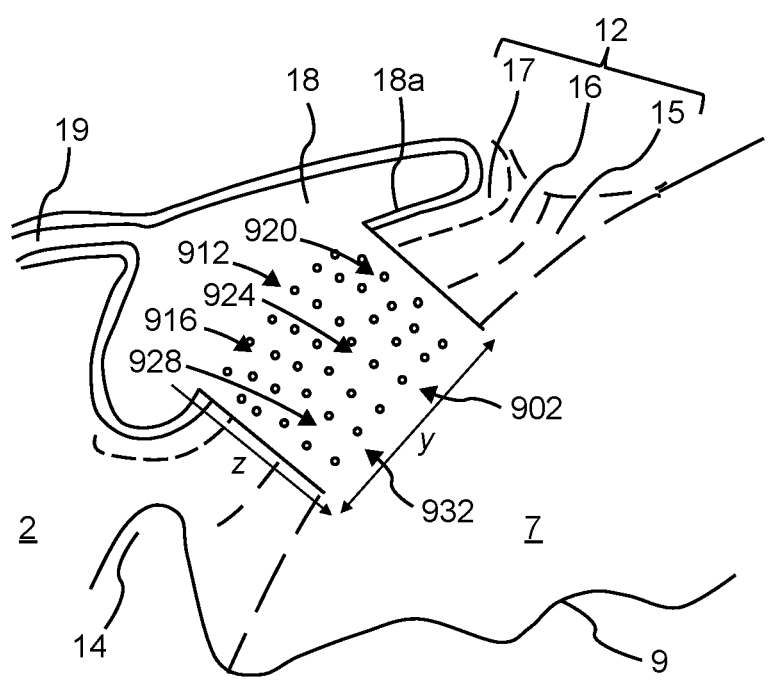

With reference to FIG. 15g, the laser scanning in multiple directions results in the photodisruption of the subsequent layer 930 of tissue and the formation of a layer of bubbles 932 at the location of the subsequent layer of tissue. Photodisruption of this subsequent layer 930 of tissue results in the formation of an opening 902 between the anterior chamber 7 and the Schlemm's canal 18, thus completing the laser treatment procedure.

Figure 16A:
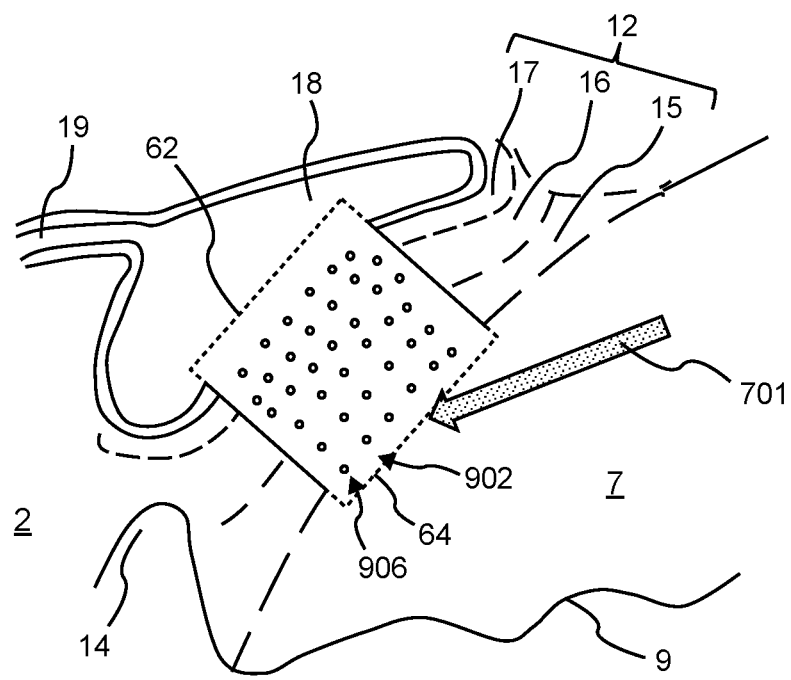
FIGS. 16a and 16b are a series of schematic illustrations of an optional laser scanning process through the opening of FIG. 15g, where the scanning begins at the end of the opening adjacent the anterior chamber and proceeds toward the Schlemm's canal.
Figure 16B:
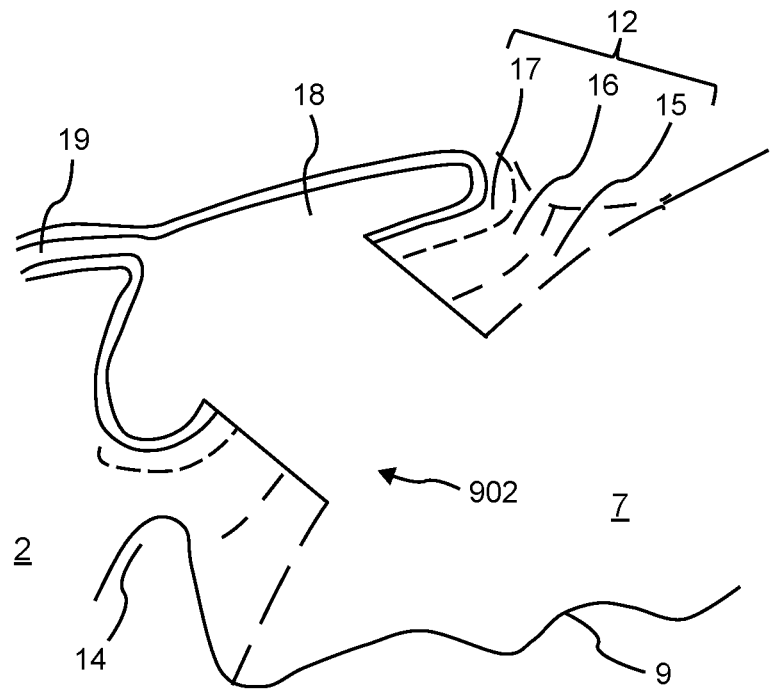

With reference to FIG. 16a, upon completion of the laser scanning the opening 902 may be partially obstructed or occluded by the gas bubbles 912, 916, 920, 924, 928 created during treatment. Thus, in accordance with embodiments disclosed herein, the direction of the laser scanning described with reference to FIGS. 15a-15g may be reversed in order to push any remaining bubbles into the Schlemm's canal 18 thereby clearing the opening 902, as shown in FIG. 16b.

Figure 17:
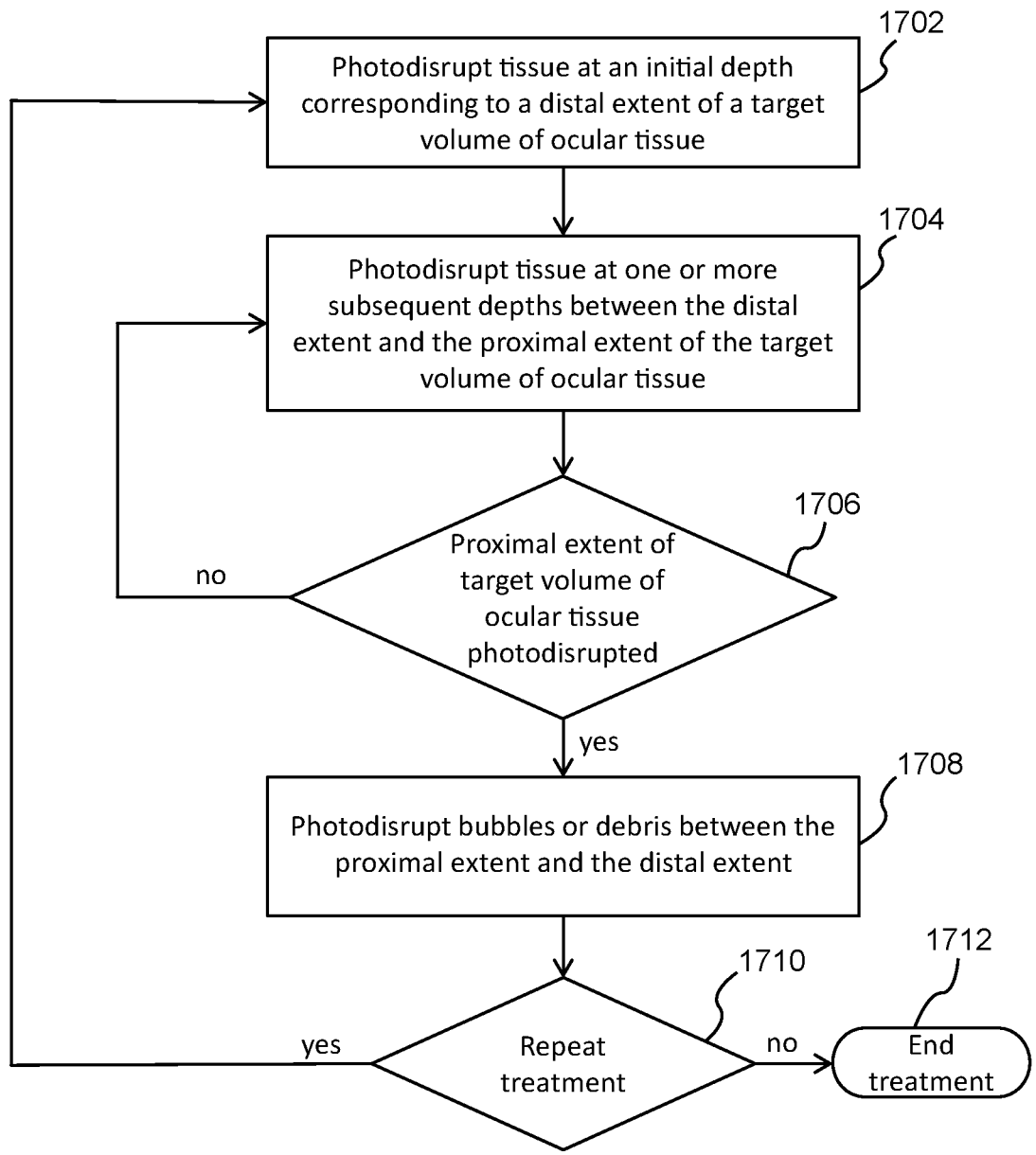
FIG. 17 is a flowchart of a method of treating a volume of ocular tissue.

FIG. 17 is a flowchart of a method of treating a target volume of ocular tissue with a laser having a direction of propagation toward the target volume of ocular tissue. With reference to FIG. 12, the target volume 60 of ocular tissue is characterized by a distal extent 62, a proximal extent 64, and a lateral extent 66. The distal extent 62 corresponds to the part or point of the target volume 60 that is most distal along the direction of propagation of the laser 701. The proximal extent 64 corresponds to the part or point of the target volume 60 that is most proximal along the direction of propagation of the laser 701. The lateral extent 66 corresponds to the distance or width w of the target volume 60 along the circumference angle.

The method, which may be performed by the integrated surgical system 1000 of FIGS. 7-10b, begins at a point in a surgical procedure where access to the irido-corneal angle has already been obtained and the target volume 60 of ocular tissue has already been identified for treatment. Systems and methods for accessing the irido-corneal angle are described in U.S. patent application Ser. No. 16/036,883, entitled Integrated Surgical System and Method for Treatment in the Irido-Corneal Angle of the Eye, the disclosure of which is hereby incorporated by reference. Systems and method for identifying volumes of ocular tissue for treatment and designing treatment patterns reference are described in U.S. patent application Ser. No. 16/125,588, entitled Non-Invasive and Minimally Invasive Laser Surgery for the Reduction of Intraocular Pressure in the Eye, the disclosure of which is hereby incorporated by reference.

At block 1702, the integrated surgical system 1000 initially photodisrupts tissue at an initial depth $d_1$ corresponding to the distal extent 62 of the target volume 60 of ocular tissue is. To this end, and with reference to FIG. 15*a*, the integrated surgical system 1000 focuses light from a femtosecond laser 701 at a spot in the tissue at the initial depth $d_1$ and applies optical energy to the tissue, which energy is at a level sufficient to photodisrupt the tissue. Optical energy is applied by scanning the laser 701 in multiple directions defining an initial treatment plane 910 at the initial depth $d_1$ to thereby photodisrupt an initial layer of tissue of the target volume of ocular tissue. With reference to FIG. 13, the scanning may be in the form of a raster scan where the laser is scanned in a first direction along the lateral extent 66, i.e., the x direction, and then slightly repositioned in a second direction. i.e., the y direction, and then scanned again along the lateral extent.

As an additional aspect of the initial photodisruption process of block 1702, the integrated surgical system 1000 may detect the distal extent 62 of the target volume of ocular tissue. To this end, in one configuration images captured by the OCT imaging apparatus 300 are processed by the control system 100 to detect the distal extent 62 of the target volume using known techniques. In another configuration, the integrated surgical system 1000 may include a multiphoton imaging apparatus (not shown) that provides a visual indication on a display of the user interface 110 that is indicative of the location of the focus of the laser 701 relative to the distal extent 62 of the target volume 60 of ocular tissue. The integrated surgical system 1000 may also determine the lateral extent 66 of the target volume 60 of ocular tissue based on OCT imaging.

At block 1704 and with reference to FIGS. 15*b*-15*f*, the integrated surgical system 1000 subsequently photodisrupts tissue at one or more subsequent depths $d_2$-$d_6$ between the distal extent 62 of the target volume 60 of ocular tissue and the proximal extent 64 of the target volume of ocular tissue is by moving a focus of the laser 701 in a direction opposite the direction of propagation of the laser. To this end, the integrated surgical system 1000 focuses light from a femtosecond laser 701 at a spot in the tissue at the one or more subsequent depths $d_2$-$d_6$ and applies optical energy to the tissue, which energy is at a level sufficient to photodisrupt the tissue. Optical energy is applied by scanning the laser 701 in multiple directions defining a subsequent treatment plane 914, 918, 922, 926, 930 at a respective different depth $d_2$-$d_6$, to thereby photodisrupt one or more subsequent layers of tissue of the target volume 60 of ocular tissue. With reference to FIG. 13, the scanning may be in the form of a raster scan where the laser is scanned in a first direction along the lateral extent 66, i.e., the x direction, and then slightly repositioned in a second direction. i.e., the y direction, and then scanned again along the lateral extent.

As an additional aspect of the subsequent photodisruption process of block 1704, the integrated surgical system 1000 may detect the proximal extent 64 of the target volume 60 of ocular tissue. To this end, in one configuration images captured by the OCT imaging apparatus 300 are processed by the control system 100 to detect the proximal extent 64 of the target volume 60 using known techniques. In another configuration, the integrated surgical system 1000 may include a multiphoton imaging apparatus (not shown) that provides a visual indication on a display of the user interface 110 that is indicative of the location of the focus of the laser 701 relative to the proximal extent 64 of the target volume 60 of ocular tissue. In yet another configuration, the integrated surgical system 1000 may include an opto-mechanical imaging apparatus (not shown) that provides a visual indication on a display of the user interface 110 that is indicative of the location of the focus of the laser 701 relative to the proximal extent 64 of the target volume 60 of ocular tissue.

At block 1706, the integrated surgical system 1000 determines if the proximal extent 64 of the target volume 60 of ocular tissue has been photodisrupted. If the proximal extent 64 has not been photodisrupted, the process return to block 1704 and the integrated surgical system 1000 repeats the photodisrupting at one or more subsequent depths until tissue at the proximal extent 64 of the target volume 60 of ocular tissue is photodisrupted.

Returning to block 1706 and with reference to FIG. 16*a*, if the proximal extent 64 has been photodisrupted, the process proceeds to block 1708 and the integrated surgical system 1000 photodisrupts tissue debris or bubbles 906 between the proximal extent 64 of the target volume 60 of ocular tissue and the distal extent 62 of the target volume by moving the focus of the laser 701 in the direction of propagation of the laser. To this end, the integrated surgical system 1000 focuses light from a femtosecond laser 701 at a spot in the volume of tissue debris or bubbles 906 at the one or more subsequent depths and applies optical energy to the tissue debris or bubbles. Optical energy is applied by scanning the laser 701 in multiple directions along one or more of the previously-scanned treatment planes 910, 914, 918, 922, 926, 930 to photodisrupt tissue debris or bubbles 906 between the proximal extent 64 and the distal extent 62 of the photodisrupted target volume 60.

At block 1710, the integrated surgical system 1000 may determine to repeat the treatment of the photodisrupted target volume 60 of ocular tissue or to end the treatment. If treatment is repeated, the process returns to block 1702, where the integrated surgical system 1000 repeats the initial photodisrupting of tissue, and then proceeds to blocks 1704 and 1706, where the system repeats the subsequent photodisrupting of tissue one or more times. If treatment is not to be repeated, the process proceeds to block 1712, where treatment ends.

Regarding the use of a multiphoton imaging apparatus to detect the distal extent 62 of the target volume of ocular tissue, or the proximal extent 64 of the target volume, such an apparatus is configured to present an image of a second harmonic light that results from an encounter between the focus of the laser 701 and tissue. When the focus of the laser 701 is not encountering tissue, the intensity of the second harmonic light is zero or very low. When the focus is encountering tissue, the intensity of the second harmonic light increases. Based on this, a distal extent 62 such as shown in FIG. 12 may be detected by first advancing the focus of the laser 701 through the trabecular meshwork 12 and the inner wall 18*a* of the Schlemm's canal and into the Schlemm's canal 18, where the focus will not encounter light and the intensity of the second harmonic light is zero or very low, and then retracting the focus back toward the inner wall 18*a* of the Schlemm's canal and detecting that the focus is at the inner wall when an increase in the intensity of the second harmonic light is noted on the display.

Regarding the use of an opto-mechanical imaging apparatus to detect the proximal extent 64 of the target volume 60 of ocular tissue, such an apparatus is configured to direct a first beam of light and a second beam of light to be incident with the target volume and to align the first beam of light and the second beam of light relative to each other and relative to the laser beam such that the first beam of light and the second beam light intersect at a point corresponding to the focus of the laser. The apparatus is also configured to capture an image of a first spot corresponding to the first beam of light, and a second spot corresponding to the second beam of light relative to the proximal extent 64 of the target volume 60 of ocular tissue. The first and second spots appear in the image as two separate visible spots on the surface of the proximal extent 64 when the focus is away from the surface, and as a single, overlapping spot when the focus is on the surface. Accordingly, the proximal extent 64 is detected when the spots overlap.

With reference to FIGS. 7-10b, a surgical system 1000 for implementing the method of FIG. 17 includes a first optical subsystem 1001 including a focusing objective 700 configured to be coupled to the eye 1, and a second optical subsystem 1002 including a laser source 200 configured to output a laser beam 201/701. The second optical subsystem 1002 also includes a plurality of components 1003 configured to one or more of focus, scan, and direct the laser beam through the focusing objective, in a direction of propagation toward the target volume of ocular tissue.

The surgical system 1000 further includes a control system 100 coupled to the second optical subsystem 1002 and configured to control the focus and scan of the laser beam 701 to photodisrupt tissue at an initial depth corresponding to the distal extent of the target volume of ocular tissue. To this end, the control system 100 is configured to focus light from a femtosecond laser source 200 at a spot in the tissue at the initial depth and then apply optical energy to the tissue, where the energy is sufficient to photodisrupt tissue. The control system 100 controls the focus and scan of the laser beam 701 during application of optical energy by being further configured to scan the laser in multiple directions defining an initial treatment plane, to thereby photodisrupt an initial layer of tissue of the target volume of ocular tissue.

The control system 100 is also configured to control the focus and scan of the laser beam 701 to photodisrupt tissue at one or more subsequent depths between the distal extent of the target volume of ocular tissue and the proximal extent of the target volume of ocular tissue by moving a focus of the laser in a direction opposite the direction of propagation of the laser. To this end, the control system 100 is configured to focus light from a femtosecond laser source 200 at a spot in the tissue at a subsequent depth and then apply optical energy to the tissue, where the energy is sufficient to photodisrupt tissue. The control system 100 controls the focus and scan of the laser beam 701 during application of optical energy by being further configured to scan the laser in multiple directions defining a subsequent treatment plane, to thereby photodisrupt a subsequent layer of tissue of the target volume of ocular tissue.

The control system 100 is also configured to control the focus and scan of the laser beam 701 to photodisrupt tissue debris or bubbles between the proximal extent of the target volume of ocular tissue and the distal extent of the target volume by moving the focus of the laser in the direction of propagation of the laser, after photodisrupting the target volume of ocular tissue. The control system 100 is further configured to control the focus and scan of the laser beam 701 to repeat the initial photodisrupting of tissue and the subsequent photodisrupting of tissue one or more times.

Figure 18:
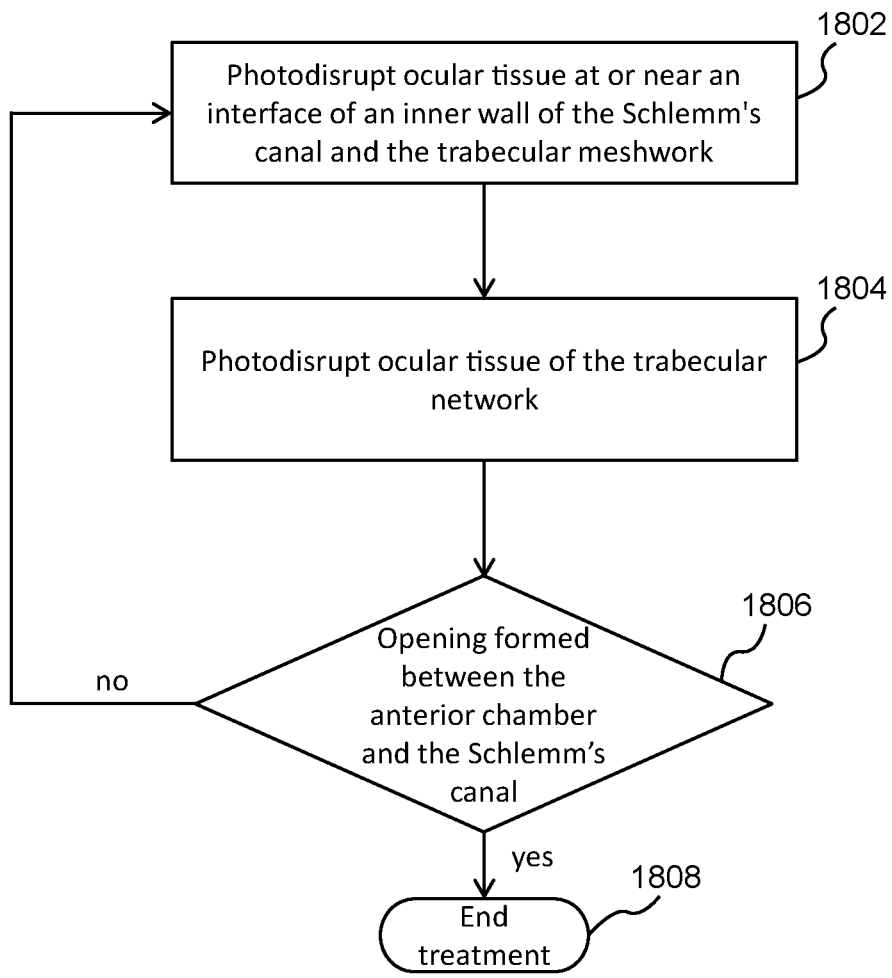
FIG. 18 is a flowchart of a method of treating an eye comprising an anterior chamber, a Schlemm's canal, and a trabecular meshwork.

FIG. 18 is a flowchart of a method of treating an eye comprising an anterior chamber, a Schlemm's canal, and a trabecular meshwork therebetween. The method, which may be performed by the integrated surgical system 1000 of FIGS. 7-10b, begins at a point in a surgical procedure where access to the irido-corneal angle has already been obtained and one or more anatomical structures of the eye that are to be treated have been located.

At block 1802 and with reference to FIGS. 15a and 15b, the integrated surgical system 1000 initially photodisrupts ocular tissue at or near an interface of an inner wall 18a of the Schlemm's canal 18 and the trabecular meshwork 12. To this end, the integrated surgical system 1000 focuses light from a femtosecond laser 701 at a spot in the ocular tissue at or near the interface of the inner wall 18a of the Schlemm's canal 18 and the trabecular meshwork 12 and applies optical energy to the tissue, which energy is at a level sufficient to photodisrupt the tissue.

As an additional aspect of the initial photodisruption process of block 1802, the integrated surgical system 1000 may detect ocular tissue at or near the interface of the inner wall 18a of the Schlemm's canal 18 and the trabecular meshwork 12. To this end, in one configuration images captured by the OCT imaging apparatus 300 are processed by the control system 100 to detect the interface of the inner wall 18a of the Schlemm's canal 18 and the trabecular meshwork 12 using known techniques. In another configuration, the integrated surgical system 1000 may include a multiphoton imaging apparatus (not shown) that provides a visual indication on a display of the user interface 110 that is indicative of the location of the focus of the laser 701 relative to the interface of the inner wall 18a of the Schlemm's canal 18 and the trabecular meshwork 12. The integrated surgical system 1000 may also determine a lateral extent 66 of ocular tissue to be photodisrupted based on OCT imaging.

At block 1804 and with reference to FIGS. 15c-15f, the integrated surgical system 1000 subsequently photodisrupts ocular tissue of the trabecular meshwork 12. To this end, the integrated surgical system 1000 focuses light from a femtosecond laser 701 at a spot in tissue of the trabecular meshwork 12 and applies optical energy to the tissue, which energy is at a level sufficient to photodisrupt the tissue.

As an additional aspect of the subsequent photodisruption process of block 1804, the integrated surgical system 1000 may detect a proximal extent of tissue of the trabecular meshwork. To this end, in one configuration images captured by the OCT imaging apparatus 300 are processed by the control system 100 to detect the proximal extent 64 of the tissue of the trabecular meshwork using known techniques. In another configuration, the integrated surgical system 1000 may include a multiphoton imaging apparatus (not shown) that provides a visual indication on a display of the user interface 110 that is indicative of the location of the focus of the laser 701 relative to the proximal extent 64 of the tissue of the trabecular meshwork. In yet another configuration, the integrated surgical system 1000 may include an opto-mechanical imaging apparatus (not shown) that provides a visual indication on a display of the user interface 110 that is indicative of the location of the focus of the laser 701 relative to the proximal extent 64 of the tissue of the trabecular meshwork At block 1806, the integrated surgical system 1000 determines if an opening is formed between the anterior chamber and the Schlemm's canal. If an opening has not been formed, the process return to block 1802 and the integrated surgical system 1000 repeats the initial photodisrupting of ocular tissue and then proceeds to block 1804 and repeats the subsequent photodisrupting of ocular tissue one or more times until an opening is formed between the anterior chamber and the Schlemm's canal. If an opening has been formed, the process proceeds to block 1808, where treatment ends.

With reference to FIGS. 7-10b, a system 1000 for implementing the method of FIG. 18 includes a first optical subsystem 1001 including a focusing objective 700 configured to be coupled to the eye 1, and a second optical subsystem 1002 including a laser source 200 configured to output a laser beam 201/701. The second optical subsystem 1002 also includes a plurality of components 1003 configured to one or more of focus, scan, and direct the laser beam through the focusing objective, toward ocular tissue.

The surgical system 1000 further includes a control system 100 coupled to the second optical subsystem 1002 and configured to control the focus and scan of the laser beam 701 to initially photodisrupt ocular tissue at or near an interface of an inner wall of the Schlemm's canal and the trabecular meshwork. To this end, the control system 100 is configured to focus light from a femtosecond laser source 200 at a spot in the ocular tissue at or near the interface of the inner wall of the Schlemm's canal and the trabecular meshwork, and then apply optical to the tissue, where the energy is sufficient to photodisrupt tissue.

The control system 100 is also configured to control the focus and scan of the laser beam 701 to subsequently photodisrupt tissue of the trabecular meshwork. To this end, the control system 100 is configured to focus light from a femtosecond laser at a spot in tissue of the trabecular meshwork, and then apply optical energy to the tissue, where the energy is sufficient to photodisrupt tissue. The control system 100 is further configured to control the focus and scan of the laser beam 701 to repeat the initial photodisrupting of ocular tissue and the subsequent photodisrupting of ocular tissue one or more times until an opening is formed between the anterior chamber and the Schlemm's canal.

The various aspects of this disclosure are provided to enable one of ordinary skill in the art to practice the present invention. Various modifications to exemplary embodiments presented throughout this disclosure will be readily apparent to those skilled in the art. Thus, the claims are not intended to be limited to the various aspects of this disclosure but are to be accorded the full scope consistent with the language of the claims. All structural and functional equivalents to the various components of the exemplary embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

It is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A system for treating a target volume of ocular tissue of an irido-corneal angle of an eye with a laser, the target volume of ocular tissue characterized by a distal extent, a proximal extent, and a lateral extent, the system comprising:
   a first optical subsystem including a focusing objective configured to be coupled to the eye;
   a second optical subsystem including a laser source configured to output a laser beam, and a plurality of components configured to one or more of focus, scan, and direct the laser through the focusing objective, in a direction of propagation toward the target volume of ocular tissue; and
   a control system coupled to the second optical subsystem and configured to control the focus and scan of the laser to:
      initially photodisrupt tissue at an initial depth corresponding to the distal extent of the target volume of ocular tissue; and
      subsequently photodisrupt tissue at one or more subsequent depths between the distal extent of the target volume of ocular tissue and the proximal extent of the target volume of ocular tissue by moving a focus of the laser in a direction opposite the direction of propagation of the laser.

2. The system of claim 1, wherein the control system is configured to control the focus and scan of the laser to repeat the photodisrupting at a plurality of different subsequent depths until tissue at the proximal extent of the target volume of ocular tissue is photodisrupted.

3. The system of claim 1, wherein the control system is further configured to control the focus and scan of the laser to photodisrupt tissue debris or bubbles between the proximal extent of the target volume of ocular tissue and the distal extent of the target volume of ocular tissue by moving the focus of the laser beam in the direction of propagation of the laser beam, after photodisrupting the target volume of ocular tissue.

4. The system of claim 1, wherein the control system controls the focus and scan of the laser during initial or subsequent photodisrupting of tissue by being further configured to:
   focus light from a femtosecond laser at a spot in the tissue at the initial depth or at the one or more subsequent depths; and
   apply optical energy to the tissue.

5. The system of claim 4, wherein the control system controls the focus and scan of the laser during application of optical energy by being further configured to:
   scan the focus of the laser in multiple directions defining a treatment plane, to thereby photodisrupt an initial layer of tissue of the target volume of ocular tissue or one or more subsequent layers of tissue of the target volume of ocular tissue.

6. The system of claim 1, wherein the control system is further configured to control the focus and scan of the laser to repeat the initial photodisrupting of tissue and the subsequent photodisrupting of tissue one or more times.

7. The system of claim 1, further comprising an imaging apparatus configured to capture images of ocular tissue, wherein the control system is coupled to the imaging apparatus and is configured to one or more of:
   detect the distal extent of the target volume of ocular tissue;
   detect the proximal extent of the target volume of ocular tissue; and
   determine the lateral extent of the target volume of ocular tissue.

8. The system of claim 7, wherein the imaging apparatus comprises at least one of an optical imaging apparatus, a multiphoton imaging apparatus, and an opto-mechanical imaging apparatus.

9. A system for treating an eye comprising an anterior chamber, a Schlemm's canal, and a trabecular meshwork therebetween, the system comprising:
- a first optical subsystem including a focusing objective configured to be coupled to the eye;
- a second optical subsystem including a laser source configured to output a laser beam, and a plurality of components configured to one or more of focus, scan, and direct the laser beam through the focusing objective, toward ocular tissue; and
- a control system coupled to the second optical subsystem and configured to control the focus and the scan of the laser beam to:
  - initially photodisrupt ocular tissue at or near an interface of an inner wall of the Schlemm's canal and the trabecular meshwork; and
  - subsequently photodisrupt ocular tissue of the trabecular meshwork.

10. The system of claim 9, wherein the control system controls the focus and scan of the laser beam during initial photodisrupting of ocular tissue by being further configured to:
- focus light from a femtosecond laser at a spot in tissue at or near the interface of the inner wall of the Schlemm's canal and the trabecular meshwork; and
- apply optical energy to the tissue.

11. The system of claim 9, wherein the control system controls the focus and scan of the laser beam during subsequent photodisrupting of ocular tissue by being further configured to:
- focus light from a femtosecond laser at a spot in tissue of the trabecular meshwork; and
- apply optical energy to the tissue.

12. The system of claim 9, wherein the control system is further configured to control the focus and scan of the laser beam to repeat the initial photodisrupting of ocular tissue and the subsequent photodisrupting of ocular tissue one or more times until an opening is formed between the anterior chamber and the Schlemm's canal.

13. The system of claim 9, further comprising an imaging apparatus configured to capture images of ocular tissue, wherein the control system is coupled to the imaging apparatus and is configured to one or more of:
- detect ocular tissue at or near the interface of the inner wall of the Schlemm's canal and the trabecular meshwork;
- detect a proximal extent of tissue of the trabecular meshwork; and
- determine a lateral extent of ocular tissue to be photodisrupted.

14. The system of claim 13, wherein the imaging apparatus comprises at least one of an optical imaging apparatus, a multiphoton imaging apparatus, and opto-mechanical imaging apparatus.

* * * * *